(12) United States Patent
Andersson et al.

(10) Patent No.: US 10,307,418 B2
(45) Date of Patent: *Jun. 4, 2019

(54) AZOLE PHARMACEUTICAL FORMULATIONS FOR PARENTERAL ADMINISTRATION AND METHODS FOR PREPARING AND USING THE SAME AS TREATMENT OF DISEASES SENSITIVE TO AZOLE COMPOUNDS

(75) Inventors: Borje S. Andersson, Houston, TX (US); Jeffrey Tarrand, Houston, TX (US); Benigno C. Valdez, Missouri City, TX (US)

(73) Assignee: Platform Brightworks Two, Ltd., Houston, TX (US)

( * ) Notice: Subject to any disclaimer, the term of this patent is extended or adjusted under 35 U.S.C. 154(b) by 1216 days.

This patent is subject to a terminal disclaimer.

(21) Appl. No.: 13/994,152

(22) PCT Filed: Dec. 16, 2011

(86) PCT No.: PCT/US2011/065422
§ 371 (c)(1),
(2), (4) Date: Oct. 1, 2013

(87) PCT Pub. No.: WO2012/083138
PCT Pub. Date: Jun. 21, 2012

(65) Prior Publication Data

US 2014/0031366 A1    Jan. 30, 2014

Related U.S. Application Data

(60) Provisional application No. 61/423,937, filed on Dec. 16, 2010, provisional application No. 61/509,154, filed on Jul. 19, 2011.

(51) Int. Cl.
*A61K 31/496* (2006.01)
*A61K 9/00* (2006.01)
*A61K 47/10* (2017.01)

(52) U.S. Cl.
CPC .......... *A61K 31/496* (2013.01); *A61K 9/0019* (2013.01); *A61K 9/0053* (2013.01); *A61K 47/10* (2013.01)

(58) Field of Classification Search
CPC .... A61K 31/496; A61K 47/10; A61K 9/0019; A61K 9/0053
See application file for complete search history.

(56) References Cited

U.S. PATENT DOCUMENTS 4,842,856 A    6/1989  Hoederath et al.
7,179,475 B1 *  2/2007  Burnett et al. ................ 424/401
(Continued)

FOREIGN PATENT DOCUMENTS

EP    0156507      10/1985
JP    63-192714    10/1988
(Continued)

OTHER PUBLICATIONS

Azole: retrived from internet: http://www.merriam-webster.com/dictionary/azole. Retrieved on Nov. 12, 2015.*
(Continued)

*Primary Examiner* — Hong Yu
(74) *Attorney, Agent, or Firm* — Parker Highlander PLLC

(57) ABSTRACT

A parenteral azole composition comprises a first solvent, made of benzyl alcohol and/or an acidified alcohol such as ethanol, and a lipophilic component such as PEG400, and the azole, or triazole, such as itraconazole or posaconazole dissolved in this first composite solvent vehicle that is essentially free of surfactants, particularly non-ionic surfactants, and has low levels of water, preferably less than 5%
(Continued)

water. The composition may be further diluted with an infusion fluid, such as normal saline or 5% or 10% dextrose in water, before infusion into an immunocompromized mammal, preferably a human. The composition is useful for the treatment and suppression of infections caused by microbes such as yeast and molds that are sensitive to azoles, but it may be extended to dissolve other pharmaceutically active agents that can be used to treat other types of infectious diseases or other ailments, such as malignant and autoimmune diseases.

27 Claims, 12 Drawing Sheets

(56) References Cited

U.S. PATENT DOCUMENTS

| | | | |
|---|---|---|---|
| 2003/0072807 A1* | 4/2003 | Wong | A61K 9/10 424/490 |
| 2004/0063722 A1 | 4/2004 | Whitefield et al. | |
| 2005/0026981 A1 | 2/2005 | Sugihara et al. | |
| 2005/0048126 A1* | 3/2005 | Rabinow | A61K 9/10 424/489 |
| 2007/0082870 A1 | 4/2007 | Buchanan et al. | |
| 2009/0253712 A1 | 10/2009 | Kovacs et al. | |
| 2009/0286799 A1* | 11/2009 | Jiang | A61K 31/00 514/252.1 |
| 2010/0197621 A1 | 8/2010 | William et al. | |
| 2010/0204293 A1 | 8/2010 | Masuda et al. | |
| 2010/0222403 A1 | 9/2010 | Marcel et al. | |
| 2012/0277249 A1* | 11/2012 | Andersson | A61K 9/0019 514/254.07 |

FOREIGN PATENT DOCUMENTS

| | | |
|---|---|---|
| JP | 01-242525 | 9/1989 |
| JP | 2002-322056 | 11/2002 |
| JP | 2008-534610 | 8/2008 |
| WO | WO 2004-014431 | 2/2004 |
| WO | WO 2004-066998 | 8/2004 |
| WO | WO 2006-105399 | 10/2006 |
| WO | WO 2008/152444 A2 * | 12/2008 |
| WO | WO 2009-031642 | 12/2009 |
| WO | WO 2010-117089 | 10/2010 |
| WO | WO 2010-120755 | 10/2010 |

OTHER PUBLICATIONS

Biotin-PEG4-NHS: retrieved from internet: http://www.chempep.com/ChemPep_Products_PEGylation_Reagents.php?id=271611.htm. Retrieved on Nov. 10, 2015.*

Polyethylene glycol: retrieved from internet: https://en.wikipedia.org/wiki/Polyethylene_glycol. Retrived on Nov. 10, 2015.*

Solutions, Suspensions and Emulsions: retrieved from internet: http://cheminnerweb.ukzn.ac.za/files/solutions,%20suspensions%20and%20emulsions.pdf. retrieved on May 14, 2016.*

Benet and Sheiner, "Pharmacokinetics: The dynamics of drug absorption, distribution, and elimination", *Goodman and Gilman's The Pharmacological Basis of Therapeutics*, Goodman et al. (Eds.), 7$^{th}$ Edition, MacMillan Publishing Co: New York, 1985. Print.

Greer, "Posaconazole (Noxafil): a new triazole antifungal agent", *Baylor Univ Med Center Proc.*, 20:188-196, 2007.

Office Communication, issued in corresponding New Zealand Application No. 613167, dated Mar. 4, 2014.

PCT International Preliminary Report on Patentability, issued in International Application No. PCT/US2011/065422, dated Jun. 27, 2013.

PCT International Search Report and Written Opinion, issued in International Application No. PCT/US2011/065422, dated Aug. 3, 2012.

Willems, et al., "Itraconazole oral solutions and intravenous formulations: a review of pharmacokinetics and pharmacodynamics", *J Clin Pharm Ther.*, 26(3):159-169, 2001.

Zhou et al., "A pharmacokinetic study of intravenous itraconazole followed by oral administration of itraconazole capsules in patients with advanced human immunodeficiency virus infection", *Clin Pharmacol.*, 38(7):593-602, 1998.

Office Action issued in Japanese Application No. 2013-544816, dated Sep. 29, 2015, and English language translation thereof.

Extended European Search Report issued in European Application No. 11849408.7, dated Jun. 6, 2014.

Office Action and Search Report issued in Chinese Application No. 2011800678245, dated Sep. 30, 2014, and English language translation thereof.

* cited by examiner

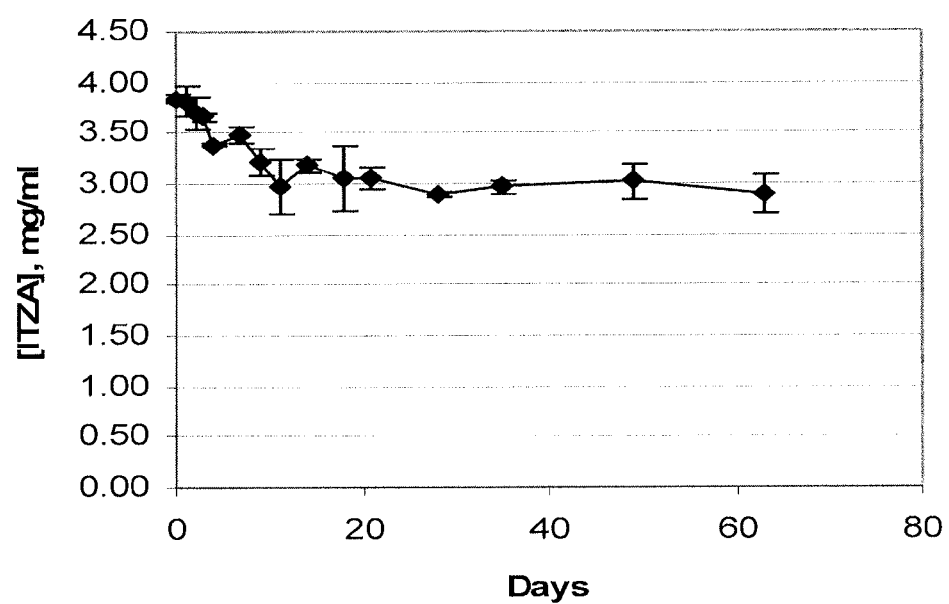
Figure 1A. Stability study of 4 mg/ml ITZA at room temp

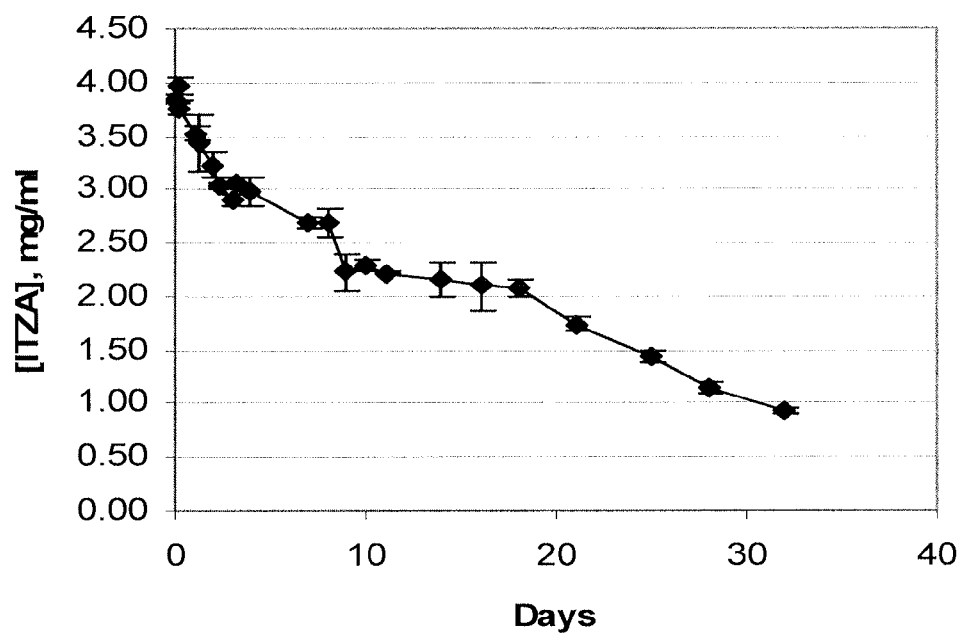
Figure 1B. Stability study of 4 mg/ml ITZA at 40 C

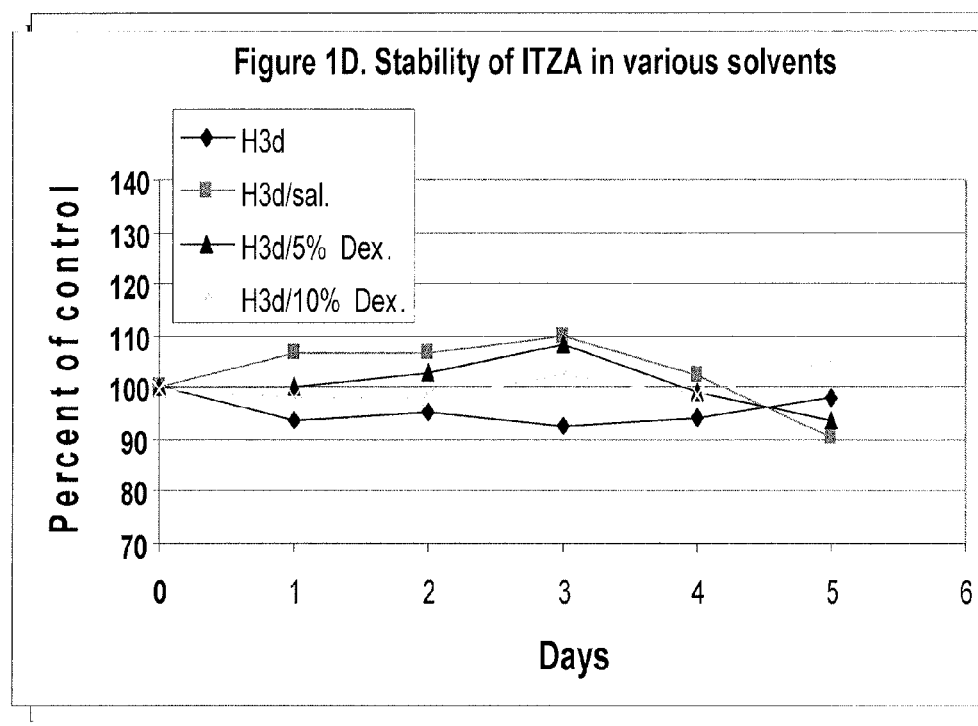

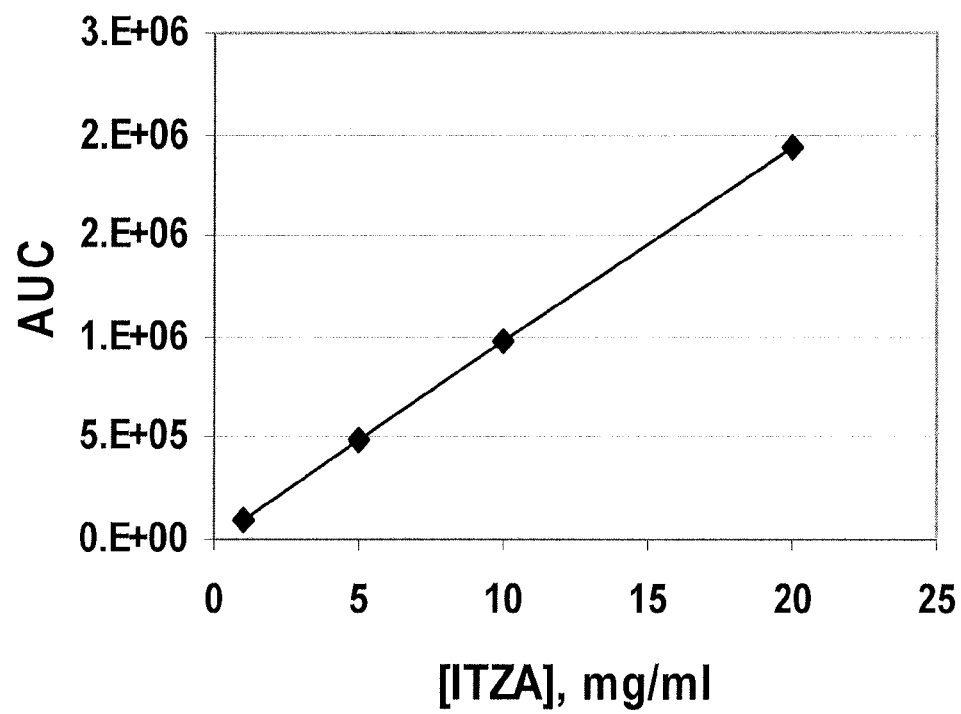
Figure 2. Standard Curve

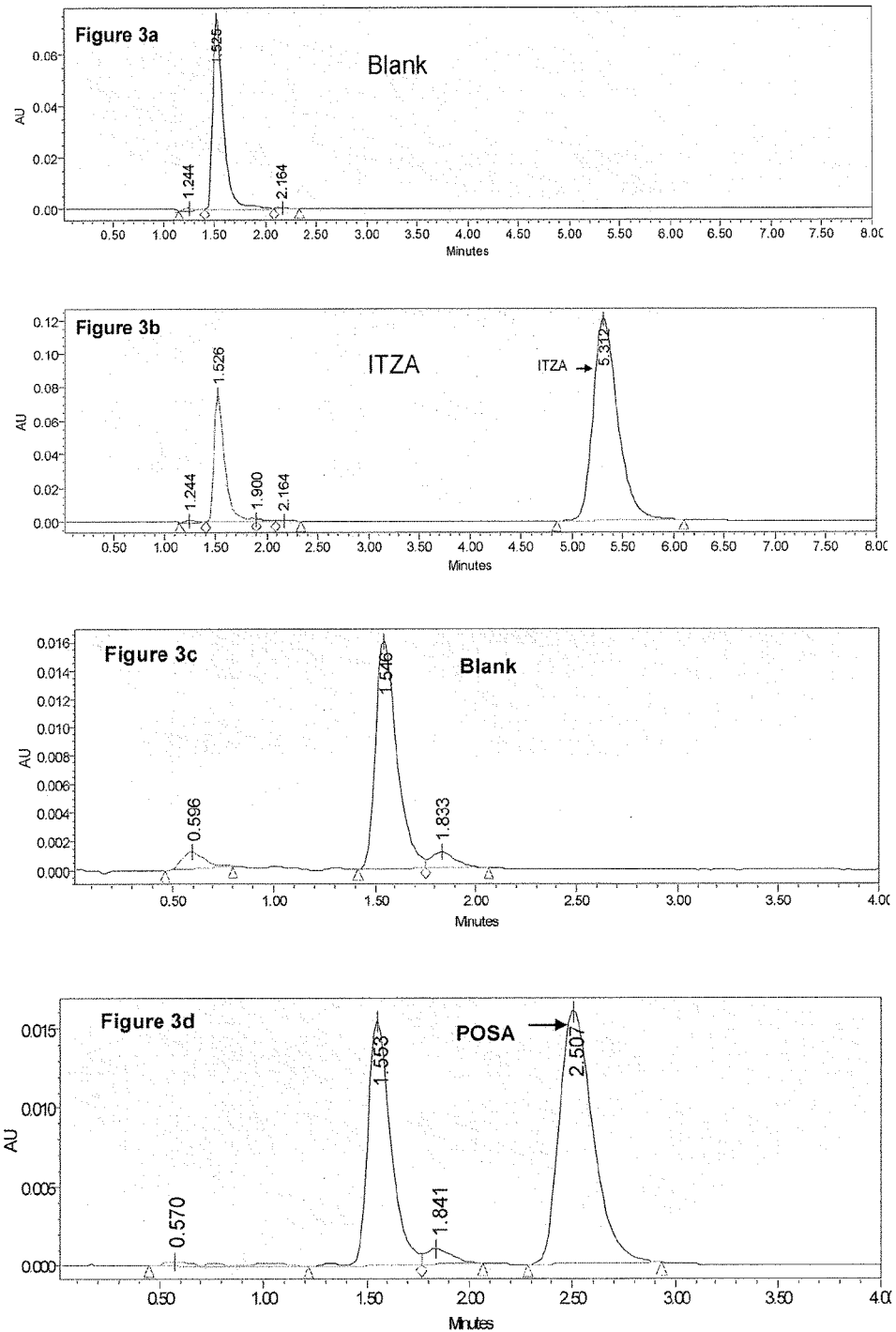

Figure 4A and B
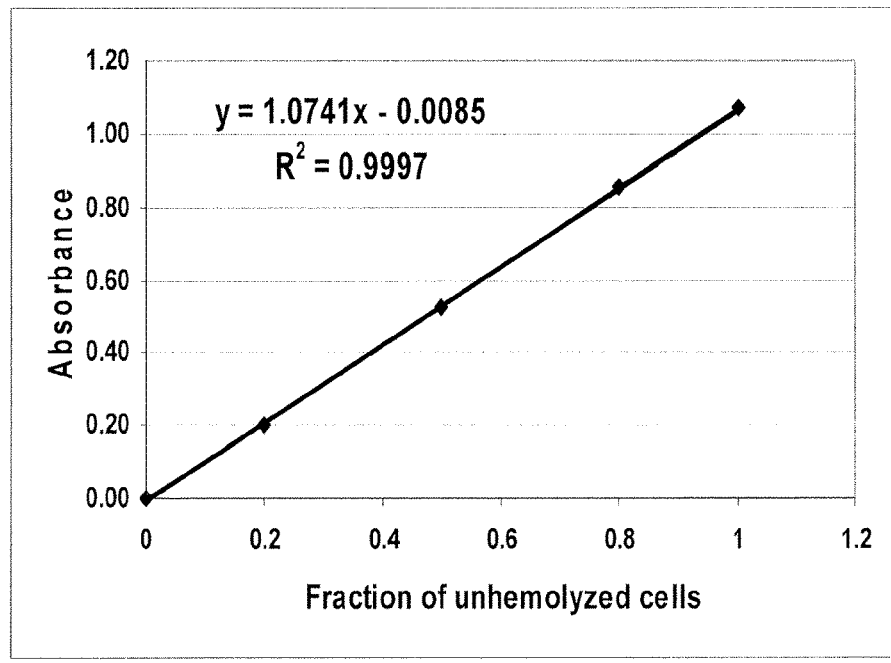
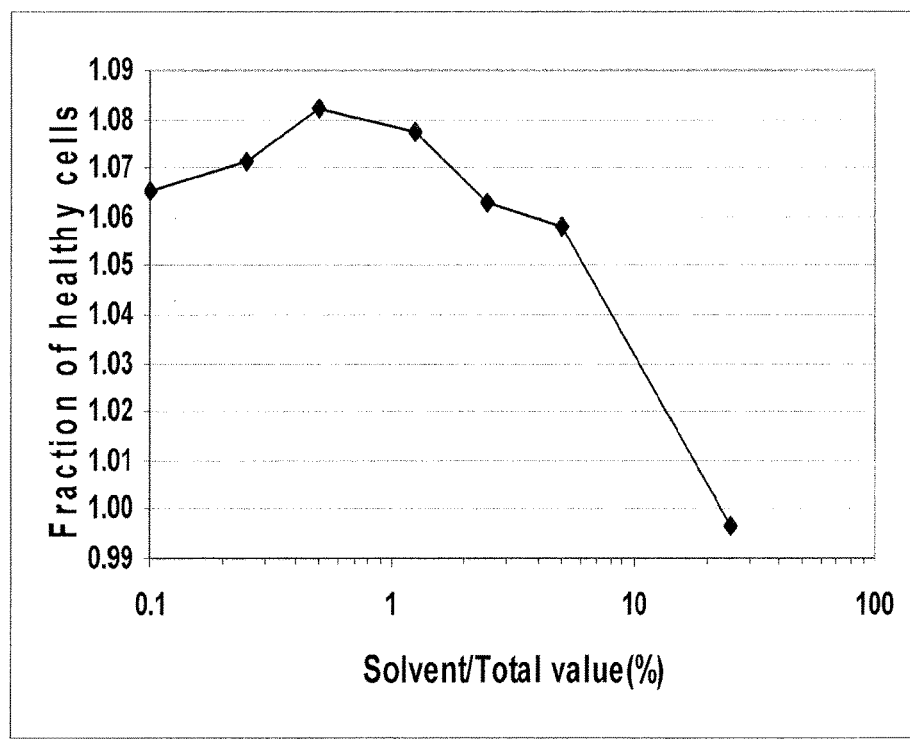

Figure 5. Effects of ITZA on the growth of *A. fumigatus* after 72-hr incubation.

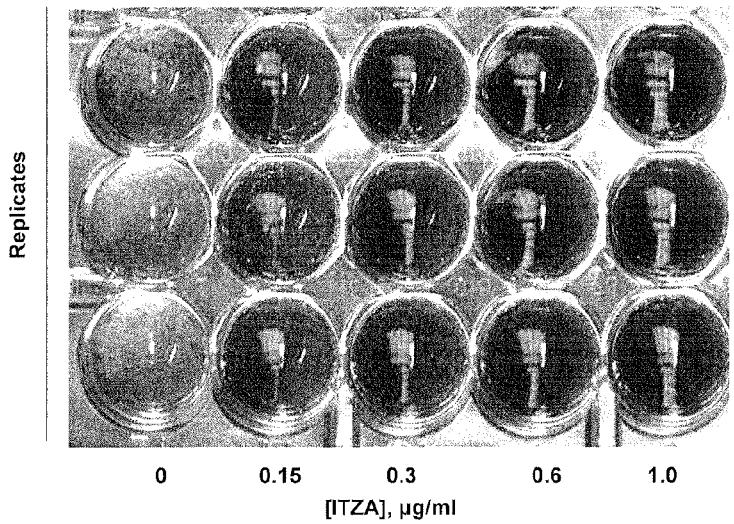

Yeasts
Tested drug dilution range: 38 µg/ml to 0.03 µg/ml

| Candida cruzei (ATCC strain 6258) | | Candida parapsilosis | |
|---|---|---|---|
| Drug | MIC | Drug | MIC |
| ITZA | 0.07 | ITZA | 0.03 |
| MBZSA | all grew | MBZSA | all grew |
| FZSA | all grew | FZSA | 1.2 |
| KZSA | 0.15 | KZSA | 0.03 |
| ITZA* | 0.15 | ITZA* | 0.07 |

ITZA* is a control lot of ITZA dissolved in DMSO as a positive control
Growth controls (negative controls, fungae grown in medium only) displayed excellent growth
Candida growth in medium with solvent vehicle without drug also displayed excellent growth.

Molds
Tested drug dilution range: 75 µg/ml to 0.07 µg/ml

| Aspergillus fumigatus (ATCC strain 90906) | | Aspergillus fumigatus (Clinical Lab Isolate) | |
|---|---|---|---|
| Drug | MIC | Drug | MIC |
| ITZA | 1.2 | ITZA | 0.6 |
| MBZSA | all grew | MBZSA | 5 |
| FZSA | all grew | FZSA | all grew |
| KZSA | 20 | KZSA | 20 |
| ITZA* | 0.6 | ITZA* | 0.3 |

ITZA* is a control lot of ITZA dissolved in DMSO as a positive control

Figure 6.
Chromatograms from plasma containing ITZA (6 B, C), and POSA (6 E, F), respectively.
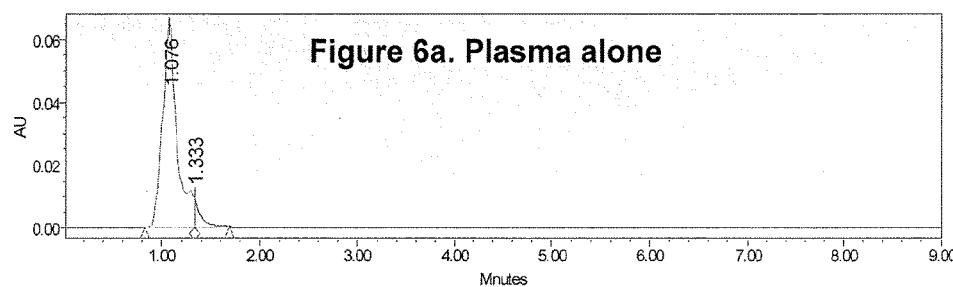
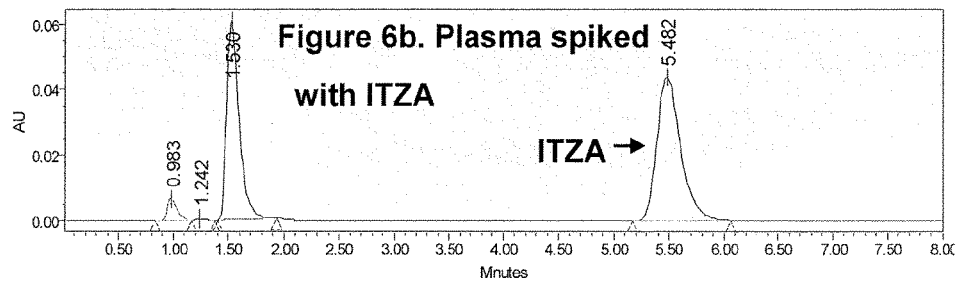
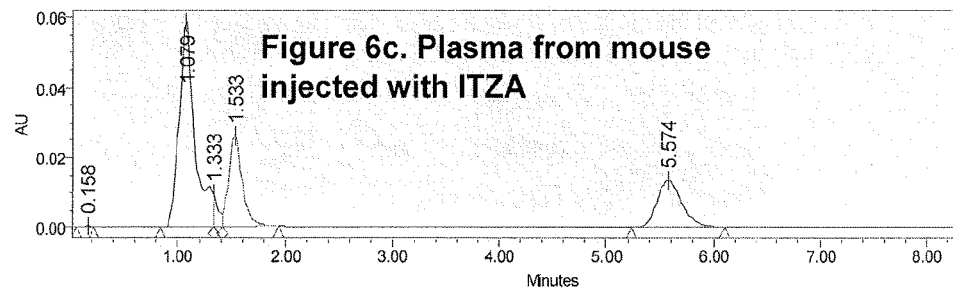

Figure 6D  Plasma alone
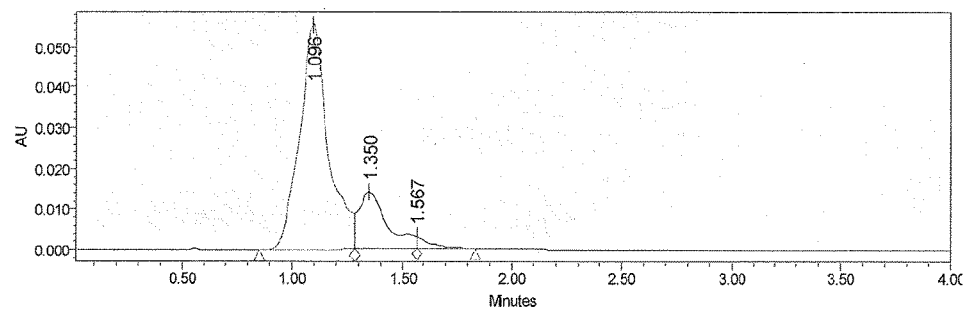
Figure 6E  Plasma spiked with POSA (POSA spike at 2.502 min.).
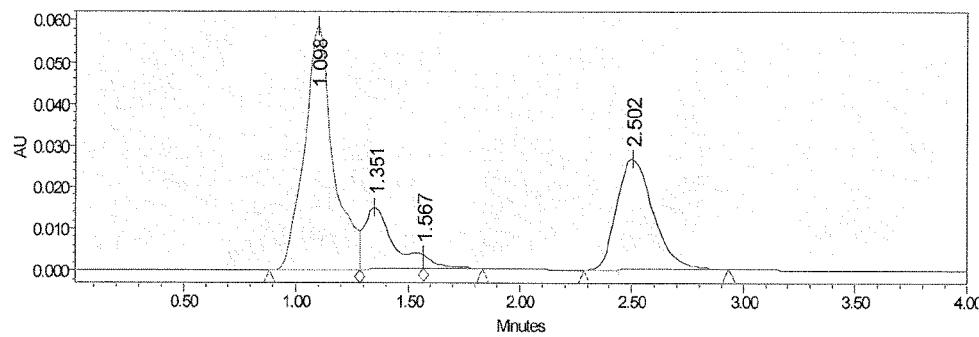
Figure 6F. Plasma from mouse injected with POSA at 5 mg/kg (POSA at 2.457 min)
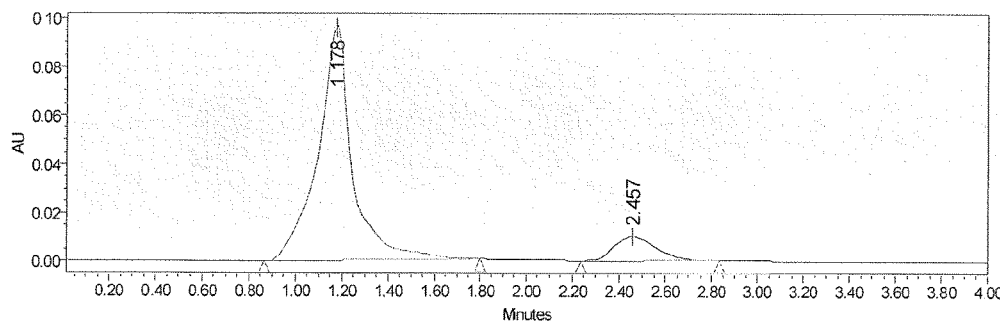

Fig 7A ITZA in H3G solvent, clearance after injections in mice at 5 mg/kg
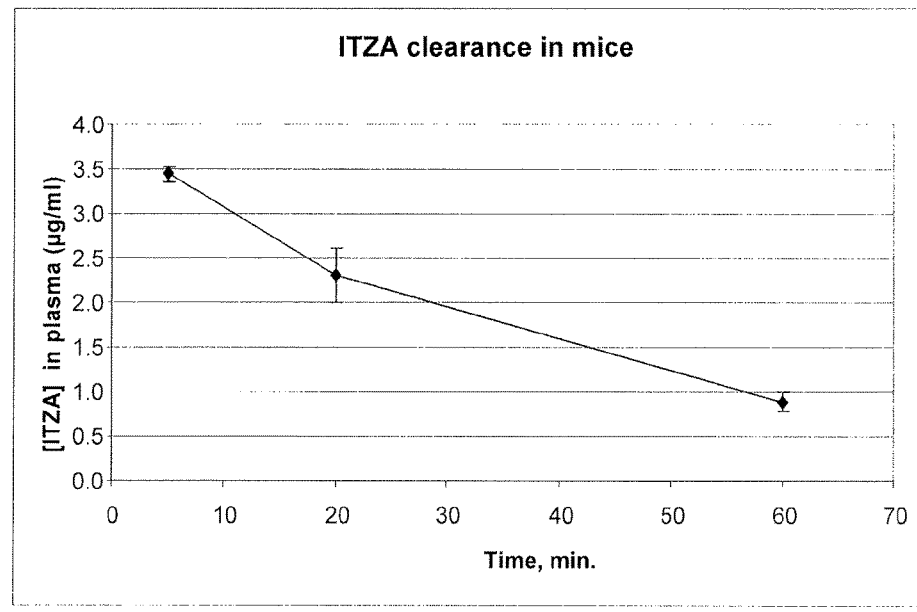
Fig. 7B POSA clearance in mice after injection of 5 mg/kg IV
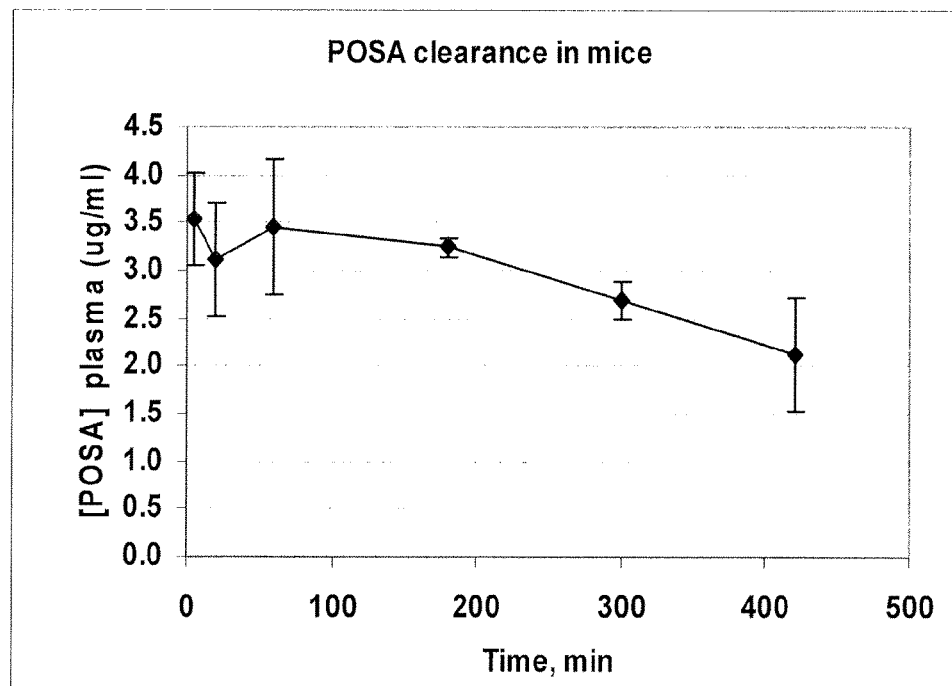

AZOLE PHARMACEUTICAL FORMULATIONS FOR PARENTERAL ADMINISTRATION AND METHODS FOR PREPARING AND USING THE SAME AS TREATMENT OF DISEASES SENSITIVE TO AZOLE COMPOUNDS

This application is a national phase application under 35 U.S.C. § 371 of International Application No. PCT/US2011/065422, filed Dec. 16, 2011, which claims the benefit of U.S. Provisional Patent Application No. 61/423,937, filed Dec. 16, 2010, and United States Provisional Patent Application No. 61/509,154, filed Jul. 19, 2011. The entire text of each of the above referenced disclosures is specifically incorporated herein by reference.

BACKGROUND OF THE INVENTION

1. Field of the Invention

The present invention is related generally to a treatment for systemic infections with yeast and mold organisms and specifically to a composition and method for parenteral administration of the general class of antiproliferative (antifungal) agents commonly referred to as azoles, and that contain itraconazole, posaconazole, voriconazole, fluconazole, ketoconazole and related compounds including, but not limited to mebendazole, in the treatment of such infections including, but not limited to fungal infections, that are sensitive to this general class of anti-infectious agents.

2. Description of Related Art

The antifungal azole agents itraconazole (ITZA) and posaconazole (POSA), that belong to the general class of agents commonly referred to as tri-azole compounds, have earned an impressive reputation for their efficacy against both yeast and various molds (Ref 1-28). The introduction of such azoles in clinical medicine has greatly improved the control of systemic fungal infections in both HIV- and non-HIV-infected immunocompromised individuals. These compounds are active against a variety of fungal infections such as aspergillosis, blastomycosis, histoplasmosis, and candidiasis, as well as fungal infections localized to the toenails and fingernails (onychomycosis), and to infections of the skin and reproductive tract (primarily referred to as "vaginal yeast infections"). They are also used for empirically and preemptively treating immunocompromised patients with fever and low white blood cell counts who are likely to develop a fungal infection after radio- or chemotherapy for malignant disease. For the purpose of this disclosure most of the data displayed and discussed will pertain to two members of the family only, since they have similar clinical shortcomings, namely itraconazole (ITZA) and posaconazole (POSA). They will be referred to collectively under the label of ITZA, unless otherwise specified.

DOSING: The usual recommended dose varies between the different members of the azole family in a single dose or two to three divided daily doses. Capsules should be taken with a full meal because lipid-containing food improves absorption.

ITZA and POSA are assumed to be rapidly absorbed from the intestinal tract. ITZA has an average bioavailability of approximately 50% while POSA has "variable" bioavailability depending on nutritional state, and a multitude of other factors that affect intestinal absorption (Ref 24, 29). Thus, intestinal absorption is highly variable, it is dependent on the intestinal microenvironment, on pH, the fat content of ingested food, and various other parameters that are only partly understood at this time (Ref 30). Unfortunately, detailed accurate data regarding intestinal absorption, as well as a thorough understanding of factors that determine this variable absorption are not available, neither are data regarding possible inter-individual variations in hepatic first-pass metabolism that further impact overall bioavailability. The impact of these factors cannot be assessed due to the absence of an IV reference formulation.

The poor solubility and physical instability of ITZA in aqueous solution has prevented the development of a useful parenteral ITZA formulation that could be used for routine clinical administration as well as for detailed pharmacological investigations. This lack of (a) solubilized IV preparation(s) impaired the development of optimal administration schedules, and it has therefore hampered the optimal clinical use of ITZA and its related analogs. Similarly, the available POSA formulation is limited to an oral suspension with a related spectrum of logistical problems that mirror those of ITZA, namely erratic and unpredictable intestinal absorption, that is dependent on intestinal pH and intestinal lipid content to allow optimal absorption, this is further compounded by varying degrees of hepatic first-pass extraction (24, 29. 30,).

Clinical frustration is mounting over the practical problems connected with these otherwise excellent antifungal agents; On one hand their broad antifungal spectrum has contributed to increasingly better control of established mold infections in immunocompromized patients and a decrease in clinically proven mold infections in high-risk patient populations when the compound(s) is/are used in a preemptive or "prophylactic" fashion, while on the other hand a lack of consistency in systemic exposure after oral dose delivery is troublesome, especially in the early treatment phase of a systemic fungal (especially mold-) infection, where it is of paramount importance to rapidly establish infection control.

Because of unreliable intestinal absorption, the use of oral antifungals is clearly suboptimal in many categories of immunodeficient patients, including those suffering from HIV-infections, in patients undergoing chemotherapy for malignant disease, and after hematopoietic stem cell transplantation where the occurrence of graft vs host disease may further impair intestinal function and therefore impede drug bioavailability. In such patients the delivery of concomitant medications that result in hypo- or achlorhydria, and/or diarrhea may also impact intestinal absorption of oral drugs. In addition, the ability to rapidly achieve therapeutic blood and tissue concentrations of antifungal agents in patients who have acquired opportunistic fungal infections is of crucial importance. For all of these reasons, the development of parenteral formulations of ITZA, POSA and later azole generations are highly desirable (Ref 31).

Based on a pharmacokinetic model that was developed from data in healthy volunteers who received single IV ITZA infusions followed by oral drug doses and subsequently validated in HIV-infected patients with opportunistic fungal infections it was concluded that an IV dosing regimen of ITZA given in a "loading phase" of 200 mg twice daily for 2 days, followed by once daily dosing of the same dose for another 5 days would produce ITZA concentrations similar to those achieved with oral ITZA given either as capsules for 28 days or as the oral solution for 14 days (Ref 32). These deliberations led to development of a microcrystalline ITZA suspension for IV administration that was introduced in clinical medicine and approved by the US FDA for use in patients with systemic fungal infections.

However, due to stability issues this formulation was voluntarily removed by the supplier from the US market in early 2009.

The problems associated with oral administration of ITZA and POSA remain unchanged, and while the need for parenteral administration forms of these azoles clinically constitutes a highly desirable, unmet need. The solubility issues have hitherto prevented the development of parenterally acceptable formulations of both these azole analogs. Further, recent pharmacokinetic data obtained with both ITZA and POSA indicate, that (oral) administration with careful monitoring of plasma concentrations will improve the control of established fungal infections. Such findings should further encourage the development of parenteral solvent systems technology for dissolving and solubilizing the drugs, such that they can be administered in high-risk patients with high precision and complete dose assurance, yet without concern for hepatic first pass elimination and a continuous need for an established optimal nutritional state and intact intestinal function of the patients to facilitate the necessary reproducible intestinal absorption that will assure acceptable systemic drug bioavailability (Ref 31). Such parenteral administration forms would also allow a more thorough investigation of various administration schedules to further improve infection-control.

Previous approaches to increase solubility in poorly-soluble drugs include the addition of surfactants. US Patent Application No. 2009/0118354 describes a formulation to solubilize docetaxel using one or more non-ionic surfactants, more preferably polysorbate 80. Similarly, US Patent Application No. 2009/0253712 discloses an aqueous solvent system for azole antifungal agents requiring a surfactant, most preferably polysorbate 80. It has been established that surfactants have toxic effects to humans (Ref 33, 34, 35). Non-ionic surfactants can alter enzyme activity, irritate skin, and modify the permeability of blood cells (33). Cremophor ELTM (polyoxyethylated castor oil), a non-ionic surfactant, was found to cause anaphylactic hypersensitivity reactions, hyperlipidaemia, and neuotoxicity (36). Polysorbate 80 has also induced severe anaphylactic reactions (37). Therefore, the formulation of a solvent system that does not require the utilization of non-ionic surfactants is beneficial.

Given the toxicity of solubilizing agents such as non-ionic surfactants, previous approaches to increase solubility in poorly-soluble drugs have also included the addition of water as a means to dilute the toxic surfactants. See, for example, US Patent Application No. 2009/0253712, which describes a solvent system for azole antifungal agents, utilizes water in the solvent system (60-80% water by volume in the more preferred embodiment), which is stated to be for the purpose of diluting out the surfactant-associated toxicity (see, e.g., paragraph [0034]). However, azoles are highly lipophilic, and the presence of water can result in a thermodynamically unstable lipid emulsion and apparently reduce the stability of the drug. Furthermore, lipid emulsions are susceptible to aggregation, flocculation, and coalescence (38). If the homogeneity of the emulsion is significantly disrupted, the drug delivery is compromised. More importantly, a disrupted emulsion can cause serious adverse reactions including plasma-derived fat embolisms (39). Thus, in the interest of preserving and optimizing treatment safety for critically ill patients, there is a need to provide parenteral drug delivery systems that are both essentially free of non-ionic surfactants and have minimal water content.

SUMMARY OF THE INVENTION

The invention relates to pharmaceutical formulations, and more particular embodiments, to parenteral formulations of azole containing pharmaceutical agents such as itraconazole (ITZA) and related anti-infectious agents. Parenteral formulations of the invention are useful for the treatment and/or suppression of systemic infections with yeast, molds and other organisms that are sensitive to compounds that belong to this general class of drugs. The parenteral formulations avoid the undesirable, erratic bioavailability and unpredictable hepatic first pass extraction, of oral preparations and in view of being truly solubilized the agents are now free from the shortcomings experienced with the intravascular delivery of particulate matter, more commonly referred to as colloidal, or micro-particular suspensions, or microcrystalline suspensions of pharmaceutically active agents.

The present invention provides pharmaceutically stable and parenterally acceptable novel formulations of azole compounds that can be utilized for the intravascular, or other systemic (or topical) treatment of infections caused by yeast, molds and other infectious agents in man and domestic animals. The formulations of the invention are based on the principle of cosolvency. Preferred cosolvent compositions of the invention are pharmaceutically acceptable, nontoxic, and stable for many hours at room temperature.

Preferred formulations according to the invention can be mixed with clinically acceptable aqueous parenteral infusion fluids, such as normal saline or dextrose in water, as final diluent(s). Preferred formulations according to the invention retain full in vitro activity in tissue cultures utilizing various strains of continuously growing molds and yeast as targets, demonstrating that our formulations according to the invention do not lose their activity when solubilized. Formulations of the invention may be used intravascularly, using the intravenous route as the prototype administration form, and have been successfully used in intravascular administration in a mouse model to demonstrate that at clinically relevant doses the resulting plasma concentrations are in an active range based on comparisons with plasma concentrations obtained in clinical routine administration of orally available formulations as reflected in the published literature. Preliminary pharmacokinetics obtained in the mouse model with (a) preferred formulation(s) of the invention has yielded detectable (fungistatic) concentrations for at least one hour after administration of various members of the azole family.

Accordingly, one embodiment of the invention is directed to an itraconazole-containing composition for parenteral use comprising itraconazole (ITZA) and a first solvent comprising (an) alcohol, such as benzyl alcohol and/or ethanol (EtOH), and an acid, such as HCl or an organic acid, to obtain a low, stable pH (preferably in a range of from 1 to 5) and finally a polyethylene glycol (PEG), preferably polyethylene glycol-400 (PEG-400), to provide/simulate a non-polar/lipophilic milieu, wherein the composition is either essentially free of non-ionic surfactants or in which such surfactants are included in very low quantities that are not toxic, and further wherein the composition has less that 5% water, preferably less than 3% water and still more preferably less than 1% water or most preferably, essentially free of water. Non-ionic surfactants that are particularly undesirable due to their toxic effects include but are not limited to Cremophor EL™, polysorbate 80, polysorbate 20, polysorbate 40, polysorbate 60, polysorbate 65, Brij 35, Brij 58, Brij 78, Brij 99, linear primary alcohol ethoxylates (such as NEODOL), Lubrol PX, Emulgen 913, nonoxynol-9, Triton X-100, polyoxyethylene-10-oleyl ether, polyoxyethylene-10-dodecyl ether, N,N-dimethyl-dodecylamine-N-oxide, and the like.

The pharmaceutically active azole agent is dissolved in the composite solvent vehicle. Prior to administration, the composition is preferably diluted with a secondary diluent comprising a readily available aqueous infusion fluid such as 0.9% sodium chloride (NS), or 5% or 10% dextrose in water (D5W and DlOW, respectively). The resulting stable, final use formulation contains the dissolved pharmaceutically active agent that, dissolved at room temperature (RT), remains stable for many hours to facilitate convenient handling and administration to the patients.

The novel solvent vehicles of the invention are not limited to ITZA and POSA, but may be used to facilitate parenteral administration of other water-insoluble drugs, preferentially members of the extended azole family. Accordingly, another embodiment of the invention includes a composition for parenteral use comprising: a water-insoluble, or poorly water-soluble/lipophilic pharmaceutically active agent; and a first solvent, the first solvent comprising (an) alcohol (such as benzyl alcohol, and/or acidified EtOH) and an acid to provide an acidic environment, and PEG, preferably PEG-400, to provide a non-proteic, lipophilic environment. The agent is dissolved in the first solvent. The composition optionally further comprises a second diluent comprising an aqueous infusion fluid to facilitate the subsequent systemic administration to a mammal, preferably a human or a (large) domestic animal.

The invention also includes a method of preparing a poorly water-soluble/lipophilic, pharmaceutically active agent for parenteral use, comprising the steps of: providing a solution of a pharmaceutically active agent, that in itself is virtually water-insoluble, in a primary solvent ("stock-solution"); and diluting the pharmaceutically active agent in the secondary, clinically acceptable infusion fluid to produce a final clinical use-formulation. In accordance with one embodiment of the invention, the primary solvent is prepared by combining PEG with an acidified alcohol such as EtOH and/or benzyl alcohol and the agent, such as ITZA or POSA, is dissolved therein. After dissolving the pharmaceutically active agent in the composite first solvent, the method may further comprise the step of mixing the primary stock formulation with a second diluent, such as an aqueous infusion fluid to facilitate its clinical administration as a clinical treatment method for a systemic ailment (such as a fungal infection), anticipated to be sensitive to azole therapy. In a particularly preferred embodiment, the ratios of PEG to alcohol is in the range of 27 to 2, and more preferably between 12 and 8, and having a pH at around 1 to 5, more preferably 3 to 4.

The invention also includes a method for treating a disease sensitive or responsive to azoles comprising: parenterally administering a therapeutically effective dissolved amount of ITZA, POSA or other azole containing pharmaceutical composition to the patient, the composition comprising: a pharmaceutically active azole derivative; a first solvent, the first solvent comprising an alcohol and an acid to provide a stable sub-physiological (low) pH, and PEG to provide a lipophilic environment, wherein the azole is dissolved in the first solvent; and a second diluent, the second diluent comprising a clinically acceptable and commonly available aqueous infusion fluid.

Still another embodiment of the invention is directed to a method for parenterally administering an azole to a mammal comprising: providing an aqueous formulation wherein a pharmaceutically active agent which in itself has very limited aqueous solubility. Through the utilization of a cosolvency approach the pharmaceutically active agent is dissolved in a stable fashion at clinically relevant concentrations to produce a primary composite solvent; dissolving the azole in the primary diluent to produce a stock formulation; mixing the stock formulation with a second diluent to form a clinically acceptable infusion fluid; and administering the infusion fluid to the mammal. Preferably, the alcohol is EtOH or benzyl alcohol and the acid is HCl and citric acid, acetic acid, or glutamic acid, while the lipophilic milieu is contributed by a PEG, such as PEG-100,-200,-300,-400,-800 and the like.

Other objects and advantages of the invention are set forth in part in the description which follows and, in part, will be obvious from this description, or may be learned from the practice of the invention.

BRIEF DESCRIPTION OF THE DRAWINGS

The following figures form part of the present specification and are included to further demonstrate certain aspects of the invention. The invention may be better understood by reference to one or more of these drawings in combination with the detailed description of specific embodiments presented herein.

FIGS. 1A-1E are graphs showing the stability of itraconazole at room temperature (FIG. 1A) and at 40° C. (FIG. 1B) in the preferred primary solvent-formulation of benzyl alcohol-acidified EtOH/PEG-400 (i.e., prototype primary solvent vehicle H3) containing 4 mg/mL ITZA. FIG. 1C shows the stability of itraconazole at room temperature in solvent H3/normal saline (1:1) (final concentration approximately 2.0 mg/ml) at room temperature. Different lots of itraconazole were solubilized and tested in repeated experiments where appropriate. The X-axis represents the time in days or hours in the respective figures, the Y-axis represents the actual drug concentration in mg/mL. FIGS. 1D and 1E shows ITZA stability in H3 variants H3D and H3G with 11.7% EtoH and devoid of benzyl alcohol.

FIGS. 1D and 1E show the stability of ITZA in H3 variant solvents H3D and H3G, respectively, in the absence or presence of NS or D5W or DlOW as final diluents.

FIG. 2 is an example of the standard curve for itraconazole concentration vs. area under the curve (AUC) (area under the curve, term used to denote the actual measured area of a peak in a chromatogram, and also for the area under the plasma concentration vs. time curve over several hours after administration of a drug to an animal or to a human, for the high-pressure liquid chromatography (HPLC) assay used in the stability studies. The X-axis shows concentration in mg/mL, and the Y-axis shows the AUC. Analogous standard curve(s) were prepared for the pharmacology studies.

FIGS. 3A-3D depict chromatograms obtained from the HPLC assay in the solubility/ stability studies described under Example 1. The injected sample volume was 10 µl. FIG. 3A blank sample, only solvent, no drug. FIG. 3B ITZA-containing sample demonstrating the ITZA-specific peak with a retention time of approximately 4.7-5.5 min under the used conditions. FIGS. 3C and 3D show the analogous chromatographic data obtained with POSA, the retention time for POSA is 2.5-3 min.

FIG. 4 is a graph showing the hemolytic potential of the final use solvent formulation (prototype H3 acidified EtOH±benzyl alcohol/PEG-400 solvent vehicle) in NS. Various combinations of Solvent:Blood were analyzed.

FIG. 5 is a photograph depicting the fungistatic activity of ITZA in the final use formulation against isolates of Aspergillus fumigatus and the accompanying Tables demonstrates the difference between different members of the azole family against various yeast and mold strains when solubilized in this solvent vehicle system.

FIGS. 6A-6F show chromatograms of plasma samples extracted as described under Example 3 and then subjected to HPLC analysis. FIG. 6A shows a blank plasma sample, FIG. 6B shows a plasma sample spiked with ITZA in the new prototype formulation, and FIG. 6C shows a chromatogram from the pharmacology study, where mice were injected with itraconazole at an estimated 5 mg/kg in a total volume of about 100 µl IV over 3-4 minutes. The sample was drawn 20 minutes after drug administration. FIGS. 6D-6F show chromatograms from the in vitro stability and in vivo experiments performed with POSA as an alternative azole.

FIGS. 7A and 7B are graphs showing the change in plasma concentration over time when 5 mg/kg ITZA (7A), and 5 mg/kg POSA (7B), respectively, were injected into mice over 3-4 min. The X-axis shows the time after dose in minutes. The Y-axis shows the concentration of ITZA or POSA, calculated in µg/mL plasma. The graphs demonstrate that clinically relevant plasma concentrations can be achieved with these formulations when injected parenterally in the described setting.

DETAILED DESCRIPTION OF THE PREFERRED EMBODIMENTS

Figure 1C:
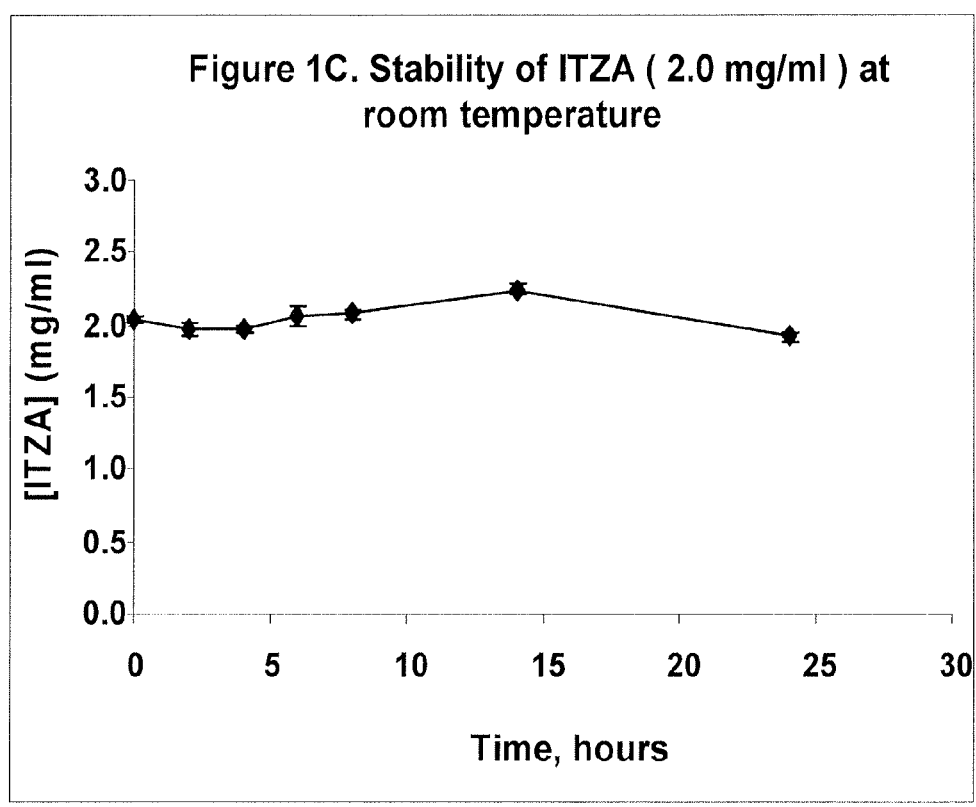

The present invention is directed to novel formulations containing anti-infectious agents, preferably belonging to the general class of compounds described as azoles, that may be administered parenterally. The invention provides for truly solubilized drugs in complex, pharmaceutically acceptable vehicles such that the dissolved drug(s) remain(s) physically and chemically stable for more than 24 hours at room temperature (RT). The invention allows for parenteral administration of the drugs in doses necessary to obtain significant, clinically relevant effects in humans and animals without undue toxicity from the proposed composite solvent vehicle(s). Preferred embodiments of the invention allow for the intravascular, or intracavitary, or intrathecal administration of ITZA and related azole agents, solubilized in alternative formulations to increase the clinical safety and efficacy of drug administration and to allow the exploration of additional, alternative, administration schedules. As a result, an improved control of infections that are sensitive to these agents may be achieved.

ITZA, as a representative example of orally administered antifungal agent(s), (tri)-azoles, has previously been extensively investigated in humans and domestic animals (Ref 1-29, 32, 40-42); the(se) drug(s) has (have) well documented anti-infectious properties in both clinical and experimental settings. However, prior to the present invention, (an) acceptable parenteral formulation(s) of solubilized ITZA, POSA and other members of this diverse family of chemicals either referred to as tri-azoles, or simply azole compounds, have not been consistently available, but parenteral administration has been accomplished by allowing the use of microcrystalline suspensions of these azoles. The variable and somewhat unreliable stability of such formulations have given varying, unpredictable results. Thus, voriconazole is currently commercially available as such a formulation, while ITZA was voluntarily withdrawn from the US market by its manufacturer, and POSA remains unavailable despite repeated attempts by the manufacturer to provide a clinically useful parenteral formulation.

Truly solubilized, parenteral formulations of ITZA and POSA would be useful as treatment of systemic infectious disorders in immunocompromised patients who for a multitude of reasons are unable to consistently take oral preparations, such as e.g. commonly experienced after (intensive) conventional chemotherapy for acute leukemia and other malignant diseases, and after (allogeneic) hematopoietic stem cell transplantation, where in the early post-transplant phase drug-related nausea, vomiting, diarrhea, and gastrointestinal mucositis, as well as administration of concomitant medications may impair oral drug bioavailability while later on the occurrence of intestinal graft-vs-host disease and its therapy may result in a similar situation. In such patients parenteral drug administration gives complete control of systemic drug delivery/pharmacokinetics of the delivered agent with an accuracy simply not attainable with an oral formulation (Ref 31). Unfortunately, ITZA is a poorly water-soluble agent with exceedingly low solubility in physiologically acceptable aqueous solvents/infusion fluids that would be compatible with human administration. Prior to the invention, the only currently available administration form is oral preparations (capsules and an oral suspension), while a previously available microcrystalline suspension for IV use was withdrawn by its supplier shortly after FDA-approval due to its unpredictable pharmaceutical behavior. To the inventors knowledge a truly solubilized form of ITZA has never been available, but only a colloidal, or microcrystalline suspension in hydroxypropyl-beta-cyclodextrin (Ref 42).

The present invention, based on the principle of cosolvency, uses a novel series of composite diluent vehicles to solubilize ITZA and POSA without affecting their anti-infectious activity. Further, the preferred solvents are, in the proposed concentrations and total doses used, nontoxic and safe for human and other intravascular administration in mammalians, most preferably in humans and domestic animals.

As discussed in the Examples below, novel vehicles have been discovered which achieve the stable, pharmaceutically acceptable solubilization of clinically active azoles, thereby making it safe to administer these drugs intravascularly. A sensitive and specific HPLC assay was initially established, which allowed the reproducible quantitation of ITZA in concentrations as low as 5-10 ng/ml. In parallel, extraction technique was developed to recover ITZA and POSA from blood plasma after IV administration. Stability studies of drugs in the newly formulated vehicles were initiated to help identify the best formulation for in vitro studies of hemolytic potential and anti-infectious activity. Finally, two of the stable new final-use formulations (ITZA and POSA were dissolved in the prototype solvent vehicle(s) and diluted with NS or dextrose in water) were injected IV in mice at 5.0 mg/kg body weight (BW). The reproducible results illustrate, that clinically relevant, fungistatic concentrations can be obtained after IV administration of these novel drug-formulations in these animals. Further, the new formulation(s) yielded plasma drug concentrations that clearly were in the anti-infectious range, demonstrating that preferred formulations of the invention may be used for intravascular treatment of infectious disorders in man and domestic animals.

As shown in the Examples, several azoles were successfully formulated for intravascular use, utilizing nontoxic composite solvent systems. Using non-toxic primary solvent vehicles mixed with the clinically acceptable infusion fluids normal saline (NS), dextrose in water at 5% and 10%, respectively (D5W and D10W), formulations that were stable for in excess of 24 hours at room temperature were produced. ITZA formulations (e.g., prior to the addition of the secondary/final aqueous diluent) are stable for several days at room temperature, are simple to handle, and provide reliable and easily controlled, consistent systemic dose administration with, and by definition retain 100% bioavailability (Ref 31).

In a preferred embodiment of the invention, ITZA is dissolved using benzyl alcohol in combination with acidified ethanol and PEG400 as the primary vehicle or solvent. These solvents are further miscible in secondary/final aqueous diluents, e.g. the routinely available aqueous infusion fluids 0.9% sodium chloride (NS), D5W, and D10W. Such terminal diluents/infusion fluids are typical examples of vehicles routinely available in any hospital. Prior to IV administration, ITZA and POSA are dissolved at concentrations of about 3-6 mg/mL and then mixed with a secondary/final diluent to a use-concentration of approximately 1.5-3 mg/mL.

While ITZA is very lipophilic, the use of an acidified alcohol/PEG400 solvent vehicle quickly dissolves it and immediately stabilizes the agent for further dilution in the secondary aqueous diluent, to be used in a similar volume. The stability of the formulation permits prolonged infusions without appreciable loss of drug activity due to physical precipitation or chemical degradation, as well as providing an opportunity to administer patients repeated doses around the clock, regardless of limitations imposed by "pharmacy operating hours", something not previously entertained in the treatment of systemic opportunistic fungal infections. This allows a very liberal view of investigating new administration schedules to maximize patient benefit from treatment with these agents, and it also allows rapid "loading" to achieve steady-state tissue drug concentrations that will assist in rapidly optimizing infection control.

As shown in the Examples, the various described composite solvent vehicles were successfully used to dissolve ITZA at concentrations ranging from less than 2 mg/mL to at least 30 mg/mL. This broad range covers the administration of doses necessary to yield antifungal concentrations in vivo to treat infections sensitive to these drugs. Further, this range is sufficient to achieve effective plasma concentrations in patients suffering systemic mold and other infections as documented by previous investigations, utilizing the orally available counterparts of the respective drugs.

The data obtained in experimental animals demonstrate that stable ITZA and POSA formulations will allow parenteral treatment of systemic fungal infections. These preparations by definition consistently provides 100% drug bioavailability (Ref 31), and it allows circumvention of both unpredictable and highly variable intestinal absorption and possible hepatic first-pass extraction that contribute to unpredictable bioavailability and suboptimal treatment efficacy. After a slow IV injection, the plasma ITZA concentrations clearly reach, and for extended time remain in, a range established as effective by the in vitro studies of its activity against various isolates of yeast and molds from human patients as well as based on studies of patients being treated for such infections with the oral counterpart agents and having subjected to pharmacokinetic studies of ITZA and POSA (Ref 32, 42, 45).

A variety of biological and chemical methods were used to demonstrate that preferred azole drug formulations are stable at approximately 4 mg/ml for several days at RT. As shown in the Examples, one such formulation is stable as a "stock formula" concentration of approximately 4 mg/mL for at least 7 days, while another formulation is stable for at least 4 days, with both of them retaining full antifungal activity as assayed in vitro against several different strains of yeast and molds. In these biological assays commercially available ITZA was dissolved in DMSO and used as a positive reference for the in vitro analysis. Further, the preferred solvent vehicle(s) is (are) nontoxic when assayed in a hemolysis assay. Two of the novel ITZA formulations were used to demonstrate that clinically relevant antifungal concentrations are maintained for at least one hour in the plasma in a mouse model after IV injection of 5 mg/kg body weight, which when combined with the known plasma half-life of approximately 10-11 hrs for ITZA and 25-35 hrs for POSA, respectively (Ref 24, 32, 42, 45), should assure the safe and effective treatment of infections with these agents.

Although the preferred embodiment of the invention uses acidified ethanol and/or benzyl alcohol, and PEG, subsequently diluted with an aqueous secondary diluent such as an infusion solution prior to systemic administration, other non-toxic solvent vehicles that are safe for human administration may be used. One preferred solvent, EtOH, that has previously been used to solubilize various pharmacologically active agents for administration in man, is routinely used as an antidote for methanol poisoning (Ref 46). No serious clinical adverse effects have been experienced from the use of such a solvent in humans in the contemplated resulting doses and concentrations. As alternative to HCl as an acidifier one could also use an organic acid such as acetic acid to drastically change the pH and thereby allow solubilization of the pharmacologically active agent. The clinical use of normal saline (NS), and dextrose in water (5-10%, w/v), as well as aqueous lipid emulsions are established, routine means to correct fluid and electrolyte balance and to supply parenteral nutrition. Normal saline and dextrose in water are also extensively used as (final) diluents for various water-soluble medications prior to IV use. Since there have been concerns about using benzyl alcohol as part of any solvent vehicles that might be used in neonates (Ref 47-51), we designed alternative composite solvent vehicles that are void of benzyl alcohol. Our extended solubility- stability- and in vivo animal experiments as well as the in vitro antifungal activity assays demonstrate the utility of these alternative, benzyl alcohol-free, solvent vehicles.

The compositions of the invention have a number of uses. As noted, preferred formulations of the invention are particularly useful in the treatment of fungal, yeast and mold infections in mammals, particularly *Candida, Aspergillus* or Mucorales infections. Certain infections, most notably those caused by *Histoplasma* Spp. and *Aspergillus* Spp. may be successfully controlled by ITZA, and in addition POSA has been of particular value in treatment of mucormycosis in immunocompromised patients. The preferred nontoxic, pharmaceutically acceptable, water-miscible, intravascular ITZA formulations of the invention eliminate the risk of treatment failure from unpredictable and erratic intestinal absorption and first-pass liver elimination/metabolism that to varying degrees characterize administration of the oral standard preparation(s). The potential benefits of using the intravascular administration route/formulation is most evident in severely ill patients with an impaired ability to swallow and therefore unable to benefit from oral nutrition such as for instance patients suffering from oral and gastrointestinal mucositis after radio- and/or chemotherapy for neoplastic disease and those suffering from gastrointestinal graft-vs-host disease after allogeneic stem cell transplantation where a similar clinical conundrum exists. The benefits are also expected to include fewer clinical side effects than that experienced with the corresponding oral drug formulation, since intravascular administration gives complete control of the bioavailability with optimized pharmacokinetics of the drugs and therefore minimizes the risk for side effects due to unwanted drug-drug interactions and treatment-failure secondary to incomplete intestinal absorption as well as accidental overdosing in patients who have an unexpectedly high intestinal absorption paired with a low metabolic drug clearance.

The novel composite solvent vehicle(s) of the invention may also be used to investigate different administration schedules (e.g., prolonged IV infusions, and repeated IV dosing) to optimize treatment outcome for azole drug-based therapy. Further, the invention makes it possible to investigate the benefits of different dose schedules of the azole drug against various systemic (infectious) diseases without the confounding adverse effects from unpredictable intestinal drug absorption and hepatic first-pass effects that in an arbitrary fashion influence the metabolism of oral azoles. Finally, it obviates the need to contend with the highly variable intestinal absorption that has been reported between patients with different underlying diseases as well as different age categories (Ref 42), and whether the patient is fed or fasting (Ref 30, 42, 45), and it finally also alleviates the need to worry about the "saturable" intestinal drug absorption that has been described after POSA administration (Ref 29). The availability of a parenteral preparation is of particular interest when more dose-intensive schedules are contemplated to control overwhelming infections in severely immunocompromised patients, such as e.g. sino-pulmonary Aspergillosis and Mucormycosis early after hematopoietic stem cell transplantation. In this particular situation, a firm control of both drug bioavailability and pharmacokinetics are of utmost importance to ensure the patient's safety through control of a drug's clinical side effects, while maximizing the chance for control of a clearly life-threatening, rapidly progressive infectious complication in a very complex medical situation, where it is of utmost importance to rapidly establish control of the infection.

Further, the stability of the new formulations makes them particularly suited for evaluating different administration schedules, including those of prolonged infusions and multiple dosing schedules, further realizing the outstanding therapeutic potential of azole drugs, particularly ITZA and POSA. The stable solubilization may also allow for intracavitary and/or intrathecal application of azole drugs as treatment of peritoneal, pleural and leptomeningeal spread of infection, although some caution has to be paid to the low pH of the infusate as well as to the (possible) content of benzyl alcohol which may contribute to meningeal inflammation that might alter a patient's seizure threshold.

Finally, as will be clear to those skilled in the art, the solvent vehicles of the invention are not limited to use with ITZA and POSA, and can be utilized in an analogous fashion to make parenteral solvent systems for other poorly water-soluble, biologically active agents, with particular emphasis on all other members of the general class of azole compounds. Exemplary antifungal azoles include a) imidazoles such as miconazole, ketoconazole, clotrimazole, econazole, omoconazole, bifonazole, butoconazole, fenticonazole, isoconazole, oxiconazole, sertaconazole, sulconazole and tioconazole, b) triazoles such as fluconazole, itraconazole, isavuconazole, ravuconazole, posaconazole, voriconazole, terconazole and c) thiazoles such as abafungin. These are examples of, but not limited to, some of the azole-containing antibiotics that can be solubilized with this technique. Other drugs that can be solubilized with this approach include, but are not limited to, hyperthyroid drugs such as carbimazole, cytotoxic agents such as epipodophyllotoxin derivatives, taxanes, bleomycin, anthracyclines, as well as platinum compounds and camptothecin analogs. They may also include other antifungal antibiotics, such as poorly water-soluble echinocandins, polyenes (e.g., Amphotericin B and Natamycin) as well as antibacterial agents, (e.g., polymyxin B and colistin), anti-viral drugs and tranquilizing/anesthetic agents such as benzodiazepines and anti-psychotics. Thus, in a broader sense, the present invention provides a method to safely solubilize and administer many poorly water-soluble, pharmacologically active agents, in addition to ITZA and POSA as examples of the diverse members of the groups of pharmaceutically active chemicals referred to as azoles, or tri-azole compounds.

Accordingly, one embodiment of the invention is directed to an azole-containing composition for parenteral use comprising the azole pharmaceutical and a first solvent comprising acidified EtOH and or benzyl alcohol as well as PEG such as PEG-400, wherein the composition is essentially free of non-ionic surfactants and comprises less than 5% water.

In still more preferred embodiments, the azole compositions will comprise less than 3% water, or less than 1% or, most preferably, will be essentially free of water. The azole drug is dissolved in the first composite solvent, and prior to administration, the composition is preferably mixed with a second diluent comprising an aqueous infusion fluid to allow for convenient clinical administration to a mammal, preferably a domestic large animal and most preferably a human.

Preferably, the alcohol such as EtOH or benzyl alcohol comprises between 1 and 25% of the first solvent and the acid comprises between 1 and 10% of the first solvent, such that a subphysiological pH is obtained in the solvent, preferably a pH of less than 4; finally the PEG more preferably comprises between 10 and 90% (v/v) of the first composite solvent.

The invention is not limited to acidified EtOH and/or benzyl alcohol with PEG. Other solvents, such as organic acids may be used to substantially alter the pH. Useful infusion fluids include, but are not limited to, normal saline and dextrose in water. Alternatively, the infusion fluid may be a lipid-based infusion emulsion fluid such as those used for parenteral nutrition.

Prior to dilution with the infusion fluid, the composition preferably comprises between 1 and 30 mg/mL of the azole drug and, more preferably, comprises between 2 mg/mL and 6 mg/mL of the agent. Preferably, the undiluted composition is stable for at least 24 hours and even more preferred stable for more than 3 days at room temperature (RT).

In a particularly preferred embodiment, the secondary diluent is an aqueous infusion fluid, e.g. normal saline and the final composition comprises between 1 mg/mL and 5 mg/mL of ITZA after mixing in the secondary, terminal, diluent. This diluted composition is stable for at least 12 hours, but preferably for more than 24 hours at RT.

The novel solvent vehicles of the invention are not limited to ITZA, but may also be used to facilitate parenteral administration of other drugs with poor aqueous solubility, including, preferably, other members of the general family of compounds commonly referred to as azoles, or tri-azole compounds, although they will also include other pharmaceutically active, poorly water-soluble agents. As noted, such drugs include, but are not limited to, cytotoxic agents such as epipodophyllotoxin derivatives, taxanes, bleomycin, anthracyclines, as well as platinum compounds. They also include antibiotics, such as poorly water-soluble polyenes (e.g., Amphotericin B and Natamycin) and other antifungal agents such as members of the group commonly referred to as echinocandins as well as antibacterial agents, (e.g., polymyxin B and colistin), anti-viral agents including, but not limited to, nucleoside analogs commonly used to treat infections such as hepatitis and retrovirus-infections. Further, they include tranquilizing, and hypnotic/anesthetic drugs such as benzodiazepines, propofol, and anti-psychotic agents. Accordingly, another embodiment of the invention includes a composition for parenteral use comprising: a water-insoluble or poorly water-soluble/lipophilic, pharmaceutically active agent and a first solvent, the first solvent comprising an acidified alcohol, a pH-lowering agent (acid), as well as polyethylene-glycol (PEG, preferably with an average molecular weight of 400 Daltons), that will contribute a lipophilic microenvironment. The pharmaceutically active agent is dissolved in the first composite solvent vehicle. The composition optionally further comprises a secondary diluent such as an aqueous infusion fluid, which will make it amenable to administration to a mammal (preferably a human or domestic animal) through an indwelling catheter.

The invention also includes a method of preparing a poorly water-soluble/lipophilic, pharmaceutically active agent for parenteral use comprising the steps of: 1) providing a composite solvent system based on the principle of cosolvency, and 2) dissolving the pharmaceutically active agent in the primary solvent vehicle to produce a stock formulation. Preferably, the primary alcohol is EtOH, the pH-lowering component is (an) acid, such as hydrochloric acid and/or citric acid, which is further compounded with PEG, and the pharmaceutically-active agent is ITZA, POSA or an alternative, later generation representative of the (tri-) azole family. The method may further comprise the step of mixing the stock formulation with a second aqueous diluent, such as an aqueous infusion fluid to facilitate safe and convenient clinical drug administration. In addition to EtOH and benzyl alcohol, other alcohols, and weaker (e.g. organic) acids such as acetic acid may be used to form the primary solvent without departing from the spirit and scope of the invention.

The invention also includes a method for treating a disease that is sensitive, or responsive, to azole-containing antifungal (e.g., ITZA/POSA) treatment comprising: parenterally administering the therapeutically effective amount of a fully solubilized azole drug composition systemically to a mammal, the composition comprising: an azole drug such as ITZA or POSA; a first solvent, the first solvent comprising an acidified alcohol and PEG, wherein the drug is dissolved in this composite solvent vehicle; and a secondary diluent, the second diluent comprising a clinically acceptable aqueous infusion fluid that will make it feasible to safely administer the dissolved drug systemically to mammals. Diseases that may be treated include, but are not limited to, fungal infections that include those caused by either yeast- or mold-species, Histoplasma spp., and neoplastic disease such as leukemia, lymphoma, Hodgkin's disease, a myeloproliferative or myelodysplastic disorder, or an autoimmune disease and an organ-transplant rejection. Preferably, the composition is administered intravascularly, however it is conceivable that the agent may also be administered intrathecally, intrapleurally, or intraperitoneally, among other routes. After mixing with or suspending in a suitable ointment base, the composition may also be applied topically, such as in the treatment of a (localized) dermal or vaginal infection. The patient can be any animal. More preferably, the animal is a mammal, and most preferably, a human.

The term "therapeutically effective amount" as used in this application means that a sufficient amount of the composition is added to achieve a desired therapeutic effect preferably starting with the first dose, or alternatively, such that a therapeutically desirable effect can be achieved after a suitable phase of repeated (systemic) administrations. The actual amount used will vary based on numerous factors, such as the type of disease, the age, sex, health, species and weight of the patient, and the use and length of use, as well as other factors known to those of skill in the art.

Still another embodiment of the invention is directed to a method for parenterally administering an azole drug such as ITZA or POSA to a patient comprising: 1) providing a composite first solvent based on the principle of cosolvency; 2) dissolving the ITZA or POSA in the primary solvent vehicle to produce a stock formulation; 3) mixing the stock formulation with a second diluent to form an infusion fluid; and 4) administering the infusion fluid to the patient. Preferably, the composite first solvent vehicle is comprised of an acidified alcohol, more preferably it is EtOH mixed with HCl and/or citric acid, and the second component is PEG400. However, in addition to EtOH, benzyl alcohol and HCl, other alcohols and acids may be used, and PEG with alternative molecular weights than the one described in our experiments can be substituted to form the primary diluent without departing from the spirit and scope of the invention.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Itraconazole Formulations Acceptable for Parenteral Administration

This example demonstrates the successful design of stable formulations of ITZA, using solvent vehicles that are non-toxic and suitable for parenteral administration. The necessary solubility/stability was calculated, and preparations were evaluated with high-pressure liquid chromatographic (HPLC) technique. The desired solubility and stability of ITZA in various solvents relevant for intravascular or intracavitary or intrathecal administration in humans and domestic animals was defined, and the solubility of ITZA in physiologically acceptable vehicles was enhanced using the rational principle of cosolvency.

Materials and Methods

Chemicals

Propylene glycol, cremophor EL, Tween 80, 6N hydrochloric acid, 2M citric acid and benzyl alcohol were obtained from Sigma (St. Louis, Mo.). Polyethylene glycol 400, 2-hydroxypropyl-beta-cyclodextrin, dextrose and acetic acid were purchased from Fisher (Pittsburgh, Pa.). Ethanol was from Decon Labs. Inc. (King of Prussia, Pa.) and intralipid was from Fresenius Kabi (Uppsala, Sweden).

HPLC Assay

The HPLC system included: an analytical column (Nova-pak C18 with 4-µm beads; 150 mm×3.9 mm; Waters Corp., Milford, Mass.), an autosampler (model Waters 717 plus autosampler, a pump (model Waters 600E system controller) set to deliver 1 mL/min and an UV detector (model Waters™

486 Tunable Absorbance detector) set at 261 nm for ITZA and POSA, 273 nm for MBZSA, 230 nm for KZSA and 259 nm for FZSA. The mobile phase for ITZA, KZSA and MBZSA was a mixture of 60% acetonitrile in $H_2O$ plus 0.05% diethylamine, sparge at 60% with helium as the degassing agent. The mobile phase for FZSA was 30% acetonitrile in $H_2O$ plus 0.05% diethylamine. A volume of 10-30 μL was injected into HPLC for quantitation of ITZA and its analogues.

Solubility Studies

ITZA and its analogues were dissolved in various solvents incubated at 37° C. for 30 minutes, cooled down to room temperature, centrifuged at 14,000 rpm for 1 min. The supernatant was analyzed using HPLC to determine the maximum solubility of ITZA and its azole analogues.

Stability Studies

To determine its long-term stability, ITZA (4 mg/ml) dissolved in solvent H3 (2.36 mg/ml citric acid, 3.42% benzyl alcohol, 68.5% PEG400, 26.55% ethanol and 0.059 N hydrochloric acid) was stored either at room temperature for 2 months or 40° C. for 1 month. The ITZA in solvent H3 was incubated in sealed tubes.

To determine its short-term stability, ITZA and its analogues in solvent H3 or solvent H3/saline (1:1) were incubated at room temperature and analyzed after 0, 2, 4, 6, 8 and 24 hours.

For both short-term and long-term stability studies, triplicate samples at various time points were analyzed quantitatively by HPLC after appropriate dilutions.

pH Assay

The pH of solvent H3/saline, with or without 2 mg/ml ITZA or its analogues, was determined. Triplicate samples from solvent alone or solvent with various drugs were analyzed.

Animal Experiment

Swiss Webster mice were used for pharmacokinetic studies of ITZA and its analogs. The dilation of the vein was accomplished by warming up the mice using a heat lamp. After dilation the mice were enclosed within a mouse-restrainer, a solution of 1.5 mg/ml ITZA or its analogs (approximately 100 μL) was slowly i.v.-injected into the mouse lateral tail vein over 3-4 min. Mice were allowed to recover and blood samples were obtained through cardiac puncture under general anesthesia with Isoflurane/oxygen by vaporizer at various time points. Plasma was obtained by centrifugation of blood sample at 3,200 rpm for 5 min. at 4° C. Plasma proteins were precipitated by adding acetonitrile (twice the volume of plasma). The mixture was vortexed for 30 seconds and centrifuged for 5 min. at 14,000 rpm. The supernatant was saved and was injected into the HPLC to determine the respective drug concentrations.

Preparation of Prototype Solvent Vehicle and Primary Stock Solution

A composite benzyl alcohol/EtOH/HCl/PEG/ITZA solution ("primary stock solution") as referenced in these Examples was prepared as follows.

In a first step the maximum ITZA solubility in various single solvents was determined. To this end, ITZA and its analogs were dissolved in various solvents, incubated at 37° C. for 30 minutes, cooled down to room temperature, centrifuged at 14,000 rpm for 1 min. The supernatant was analyzed using HPLC to determine the maximum solubility of the respective agent. The results are shown in Table 1 below.

TABLE 1

Maximum solubility of Itraconazole in various individual solvents

|  | mg/mL |
|---|---|
| Acetic acid | 144.34 |
| 50% Acetic acid | 12.92 |
| 25% Acetic acid | 0.30 |
| 10% Acetic acid | 0.86 |
| Normal saline | 0.48 |
| Polyoxyethylated castor oil | 0.89 |
| Propylene glycol | 0.14 |
| 2M citric acid | 3.22 |
| Ethanol | 0.41 |
| 6N HCl | 7.41 |
| PEG 400 | 2.51 |
| PEG 300 | 1.81 |
| PEG 200 | 1.45 |
| Intralipid | 0.15 |
| Benzyl alcohol | >128.26 |

In a second step, the solubility of ITZA in a composite solvent vehicle (H3) was determined.

Solvent H3

| Components | final concentrations |
|---|---|
| Citric acid | 2.36 mg/mL |
| Benzyl alcohol | 3.42% |
| PEG 400 | 68.5% |
| EtOH | 26.55% |
| HCl | 0.059N |

The maximum solubility of ITZA in the benzyl alcohol containing solvent H3 at room temp was determined to be approximately 31.4 mg/mL.

In an expansion of this phase, maximum solubility of ITZA in several composite solvents was determined according to the cosolvency principle.

Solvent B

| Components | final concentrations |
|---|---|
| Citric acid | 2 mg/mL |
| Benzyl alcohol | 2.9% |
| Tween 80 | 8% |
| PEG 400 | 58% |
| EtOH | 30.5% |
| HCl | 0.05N |

Maximum solubility of Itraconazole in solvent B was 29 mg/mL.

Solvent J

| Components final concentrations | | J1 | J2 | J3 | J4 | J5 |
|---|---|---|---|---|---|---|
| Citric acid | 2 mg/mL | | | | | |
| Benzyl alcohol | 2.9% | | | | | |
| 10% hydroxypropyl-β-cyclodextrin | | 7% | 10% | 15% | 20% | 25% |
| | (10% cyclodextrin, v/v, is referred to as 100%) | | | | | |
| PEG 400 | 58% | | | | | |
| EtOH | 30.5% | 27.5% | 22.5% | 17.5% | 12.5% | |
| HCl | 0.05N | | | | | |

Solubilities of Itraconazole in solvent J's were:

| Solvent | ITZA (mg/mL) |
|---|---|
| J1 | 18.13 |
| J2 | 15.99 |
| J3 | 10.11 |
| J4 | 6.09 |
| J5 | 3.54 |

Solvent K

| Components | final concentrations |
|---|---|
| Benzyl alcohol | 1.9% |
| Intralipid | 4.9% |
| PEG 400 | 39.2% |
| EtOH | 20.6% |
| Acetic acid | 33.3% |

Maximum solubility of Itraconazole in solvent K at RT was 11.1 mg/mL.

Solvent L

| Components | final concentrations |
|---|---|
| HP-beta-cyclodextrin | 32% |
| PEG 400 | 60% |
| H2O | 8% |
| HCl | 0.05N |

Maximum solubility of ITZA in solvent L was 5 mg/mL.

Azole solubilities in H3-Variant vehicles without benzyl alcohol (H3D and H3G) were carried out and the results compiled in Table 2. The H3D and H3G formulations were as follows:

Solvent H3D and H3G

| Solvent Composition | H3D | H3G |
|---|---|---|
| Citric acid (mg/mL) | 2.36 | 2.36 |
| Ethanol (%) | 17.7 | 11.8 |
| HCl | 0.059 | 0.059 |
| PEG-400 | 80.7 | 86.6 |

TABLE 2

HPLC conditions
Flow mL/min, 60% sparge.
10 ul injected into HPLC

| Solvent | Drug | λ | RT | AUC | [Drug] mg/mL | Average mg/mL |
|---|---|---|---|---|---|---|
| H3D | ITZA | 261 nm | 4.737 | 9580865 | 19.1 | 19.0 |
|  |  |  | 4.737 | 9472072 | 18.9 |  |
| H3G |  |  | 4.738 | 9631929 | 19.2 | 19.3 |
|  |  |  | 4.739 | 9718954 | 19.4 |  |
| H3D | KZSA | 230 nm | 2.627 | 5138394 | 15.4 | 15.3 |
|  |  |  | 2.631 | 5082173 | 15.2 |  |
| H3G |  |  | 2.634 | 4954869 | 14.8 | 14.9 |
|  |  |  | 2.632 | 5034867 | 15.1 |  |
| H3D | MBZSA | 273 nm | 1.286 | 3368622 | 6.4 | 6.4 |
|  |  |  | 1.287 | 3381501 | 6.5 |  |
| H3G |  |  | 1.287 | 3105982 | 5.9 | 5.9 |
|  |  |  | 1.286 | 3110974 | 5.9 |  |
| H3D | FZSA | 259 nm | 1.842 | 774441 | 38.6 | 36.1 |
|  |  |  | 1.846 | 673647 | 33.5 |  |
| H3G |  |  | 1.846 | 569780 | 28.4 | 30.3 |
|  |  |  | 1.849 | 647381 | 32.2 |  |

TABLE 2-continued

HPLC conditions
Flow mL/min, 60% sparge.
10 ul injected into HPLC

| Solvent | Drug | λ | RT | AUC | [Drug] mg/mL | Average mg/mL |
|---|---|---|---|---|---|---|
| H3D | POSA | 261 nm | 2.489 | 3399423 | 33.8 | 35.34 |
|  |  |  | 2.491 | 3527182 | 35.08 |  |
|  |  |  | 2.493 | 3733502 | 37.14 |  |
| H3G |  |  | 2.494 | 3080892 | 30.62 | 32.17 |
|  |  |  | 2.496 | 3405758 | 33.86 |  |
|  |  |  | 2.496 | 3222914 | 32.04 |  |

FZSA; Fluconazole, ITZA; Itraconazole, MBZSA; Mebendazole, KZSA; Ketoconazole, POSA; Posaconazole.

Conclusions:

Based on these experiments under standardized conditions it was concluded that:

1) The highest consistent solubility, and stability, of ITZA at RT was found in the system H3 variants, where
2) Itraconazole was preferably dissolved in a composite solvent at low, subphysiological pH, necessitating the inclusion of an acidic alcohol component in the solvent vehicle.
3) The balance up to 100% v/v would benefit from inclusion of a physiologically acceptable alcohol such as EtOH, and
4) With inclusion of benzyl alcohol in the vehicle a higher stable solubility was achieved.
5) Next, the solvent vehicle would benefit from inclusion of PEG-400 to mimic a lipophilic environment as a carrier,
6) Finally, the preferred composite solvent vehicles should allow a final dilution step with a clinically acceptable infusion fluid, including but not limited to, normal saline or dextrose in water.

Stability Investigations

In the next step the stability of ITZA (at approximately 4 mg/mL) in a preferred composite solvent at a clinically relevant stock concentration by itself, and after dilution with a similar volume of a clinically acceptable infusion fluid, was determined at room temperature.

Table 3A below sets forth the results of the stability studies at room temperature, and Table 3B lists the results of the stability at 40° C.

TABLE 3A

Stability of ITZA (approximately 4 mg/mL) in the parent solvent H3 at room temperature.

| Time | ITZA (mg/mL) | Stability (%) |
|---|---|---|
| 0 | 3.84 | 100 |
| 24 hrs | 3.81 | 99 |
| 48 hrs | 3.69 | 96 |
| 72 hrs | 3.66 | 95 |
| 96 hrs | 3.38 | 88 |
| 7 days (1 w) | 3.48 | 91 |
| 9 days | 3.22 | 84 |
| 11 days | 2.97 | 77 |
| 14 (2 w) | 3.18 | 83 |
| 18 days | 3.05 | 80 |
| 21 (3 w) | 3.05 | 79 |
| 28 (4 w) | 2.89 | 75 |
| 35 (5 w) | 2.96 | 77 |
| 49 (7 w) | 3.02 | 79 |
| 63 (9 w) | 2.89 | 75 |

TABLE 3B

Accelerated stability of ITZA (approximately 4 mg/mL) in solvent H3 at 40° C.

| Time | ITZA (mg/mL) | Stability (%) |
|---|---|---|
| 0 | 3.84 | 100 |
| 3 hr | 3.98 | 104 |
| 6 hr | 3.76 | 98 |
| 24 hr | 3.52 | 92 |
| 30 hr | 3.43 | 89 |
| 48 hr | 3.23 | 84 |
| 54 hr | 3.04 | 79 |
| 72 hr | 2.91 | 76 |
| 78 hr | 3.05 | 80 |
| 4 days | 2.99 | 78 |
| 7 days | 2.68 | 70 |
| 8 days | 2.68 | 70 |
| 9 days | 2.23 | 58 |
| 10 days | 2.28 | 59 |
| 11 days | 2.21 | 58 |
| 14 days | 2.16 | 56 |
| 16 days | 2.10 | 55 |
| 18 days | 2.09 | 54 |
| 21 days | 1.74 | 45 |
| 25 days | 1.43 | 37 |
| 28 days | 1.15 | 30 |
| 32 days | 0.93 | 24 |

The foregoing data is compiled and shown graphically in FIGS. 1A and 1B, respectively.

Table 4 below shows results obtained for the stability of Itraconazole in solvent H3/normal saline (1:1) (final concentration approximately 2.0 mg/mL) at room temperature (RT) and, again, the data is shown graphically in FIG. 1C.

TABLE 4

| Time (hrs) | ITZA (2.0 mg/mL) | Stability (%) |
|---|---|---|
| 0 | 2.04 | 100 |
| 2 | 1.97 | 97 |
| 4 | 1.97 | 97 |
| 6 | 2.06 | 101 |
| 8 | 2.07 | 102 |
| 14 | 2.25 | 109 |
| 24 | 1.92 | 93 |

Conclusion: Using normal saline as final dilution solution, ITZA at 2 mg/mL is stable to more than 90% for at least 24 hours at RT.

Table 5 shows the compositions of different solvent H3 variants.

TABLE 5

| H3 solvents | H3 | H3A | H3B | H3C | H3D | H3G |
|---|---|---|---|---|---|---|
| citric acid (mg/mL) | 2.36 | 2.36 | 2.36 | 2.36 | 2.36 | 2.36 |
| Benzyl alcohol (%) | 3.42 | 0 | 0 | 0 | 0 | 0 |
| PEG400 (%) | 68.50 | 71.8 | 74.8 | 77.7 | 80.7 | 86.6 |
| EtOH (%) | 26.55 | 26.55 | 23.6 | 20.6 | 17.7 | 11.8 |
| HCl (N) | 0.059 | 0.059 | 0.059 | 0.059 | 0.059 | 0.059 |

Table 6 shows the stability studies and results of ITZA in various H3 solvent vehicles.

TABLE 6

| H3D | | RT | AUC | mg/mL | average | Stability % |
|---|---|---|---|---|---|---|
| 4 mg/mL | 0 hr | 4.479 | 449672 | 3.67 | 3.53 | 100 |
| | | 4.785 | 402066 | 3.29 | | |
| | | 4.79 | 445398 | 3.64 | | |
| | 2 hr | 4.796 | 456125 | 3.72 | 3.62 | 102 |
| | | 4.795 | 438574 | 3.58 | | |
| | | 4.793 | 434752 | 3.55 | | |
| | 4 hr | 4.826 | 425075 | 3.47 | 3.55 | 101 |
| | | 4.827 | 443570 | 3.62 | | |
| | | 4.836 | 436146 | 3.56 | | |
| | 6 hr | 4.855 | 420642 | 3.44 | 3.50 | c99 |
| | | 4.855 | 448469 | 3.66 | | |
| | | 4.883 | 414950 | 3.39 | | |
| | 8 hr | 4.904 | 431148 | 3.52 | 3.49 | 99 |
| | | 4.899 | 410046 | 3.35 | | |
| | | 4.906 | 439278 | 3.59 | | |
| | 24 hr | 5.025 | 421172 | 3.44 | 3.44 | 97 |
| | | 5.028 | 428925 | 3.50 | | |
| | | 5.031 | 412739 | 3.37 | | |

| Solvent H3G | Time, hr | RT*, min | AUC | [ITZA] mg/mL | Avrge [ITZA] mg/mL | Stability % |
|---|---|---|---|---|---|---|
| | 0 | 4.934 | 436392 | 3.56 | 3.50 | 100 |
| | | 4.926 | 427328 | 3.49 | | |
| | | 4.928 | 422232 | 3.45 | | |
| | 2 | 4.955 | 469614 | 3.83 | 3.77 | 108 |
| | | 4.957 | 451645 | 3.69 | | |
| | | 4.959 | 463700 | 3.78 | | |
| | 4 | 4.974 | 449754 | 3.67 | 3.65 | 104 |
| | | 4.975 | 442904 | 3.62 | | |
| | | 4.982 | 446950 | 3.65 | | |
| | 6 | 5.008 | 428473 | 3.50 | 3.52 | 101 |
| | | 5.007 | 421334 | 3.44 | | |
| | | 5.014 | 443857 | 3.62 | | |
| | 8 | 5.061 | 441077 | 3.60 | 3.42 | 98 |
| | | 5.06 | 398111 | 3.26 | | |
| | | 5.065 | 416459 | 3.40 | | |
| | 24 | 4.754 | 450275 | 3.68 | 3.59 | 103 |
| | | 4.755 | 427042 | 3.49 | | |
| | | 4.761 | 443023 | 3.62 | | |

RT*, Retention Time

Figure 1E:
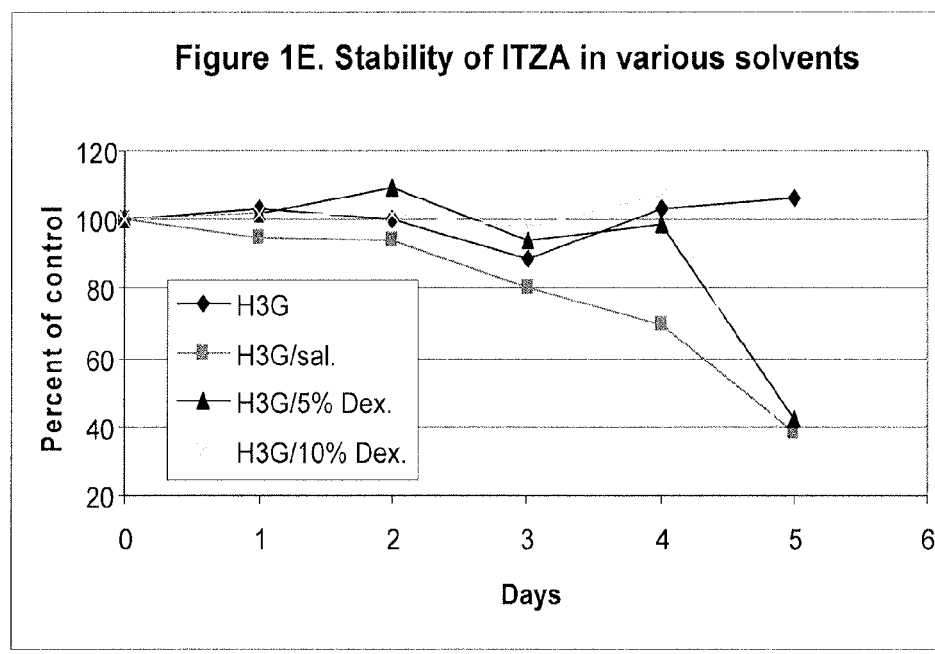

Examination of alternative final diluents (NS, D5W, D10W) on the stability of ITZA in solution. Table 7A below sets forth the azole solubility and stability in H3 variants, i.e. different composite solvent vehicles with varying amounts of EtOH, in the absence of benzyl alcohol. FIG. 7A shows the stability of ITZA in H3D with 17.7% EtOH in the absence of benzyl alcohol and Table 7B shows ITZA stability in H3 variant H3G, with 11.7% EtOH, and void of benzyl alcohol. The Tables 7A and 7B show data compiled graphically in FIGS. 1D and 1E.

TABLE 7A

| | ITZA | | | |
|---|---|---|---|---|
| Time Days | H3D | H3D/sal. | H3D/5% dex. | H3D/10% Dex. |
| 0 | 100 | 100 | 100 | 100 |
| 1 | 94 | 107 | 100 | 98 |
| 2 | 95 | 107 | 103 | 98 |
| 3 | 93 | 110 | 108 | 102 |
| 4 | 94 | 102 | 99 | 99 |
| 5 | 98 | 90 | 93 | 105 |

TABLE 7B

| Time Days | H3G | H3G/sal. | H3G/5% Dex. | H3G/10% dex. |
|---|---|---|---|---|
| 0 | 100 | 100 | 100 | 100 |
| 1 | 103 | 95 | 102 | 102 |
| 2 | 100 | 94 | 109 | 102 |
| 3 | 89 | 80 | 94 | 98 |
| 4 | 103 | 70 | 99 | 107 |
| 5 | 106 | 38 | 42 | 31 |

Table 8 below shows the analysis of a standard curve for ITZA for the stability experiments above, and the data are set forth graphically in FIG. 2.

TABLE 8

11.8.2010
standard [ITZA]

| | RT | AUC | average |
|---|---|---|---|
| 20 mg/mL | 4.879 | 2577682 | 2504326 |
| | 4.883 | 2551820 | |
| | 4.886 | 2383477 | |
| 10 mg/mL | 4.883 | 1356911 | 1285407 |
| | 4.888 | 1197158 | |
| | 4.886 | 1302151 | |
| 5 mg/mL | 4.839 | 598440 | 589708 |
| | 4.846 | 619476 | |
| | 4.846 | 551207 | |
| 1 mg/mL | 4.853 | 118515 | 125813 |
| | 4.857 | 116128 | |
| | 4.892 | 142795 | |

Calculation of Final Desired Solubility.

A Clinically and pharmaceutically relevant solubility range for ITZA was calculated by extrapolation from doses known to have significant anti-fungal efficacy in man. Such clinical studies have been conducted using the FDA-approved oral preparation. The utilized ITZA treatment schedules typically prescribe an oral dose in the range of 200-500 mg once or twice daily until desired anti-fungal effect is obtained. Commonly an initial loading dose, or pulses, of higher doses may be administered two-three times daily for several days, followed by a lower daily maintenance dose (Ref 29, 42). The clinically most effective/optimal ITZA dose schedule is not known, but based on an apparent terminal half-life of about 10-12 hours it has been commonly assumed that once or twice daily (maintenance) dose administration is sufficient to achieve desired antifungal effects. It is likely that, in similarity with other antimicrobial agents and in particular with POSA, 1) there is a dose/plasma/tissue concentration-effect relationship to obtain optimal anti-fungal (anti-infective) activity, and 2) that there will be dose-schedule dependency relative to both adverse events and anti-infectious efficacy. In reference to POSA and the need for repeated "loading doses" for 2-3 days (or about 60 hours) to achieve a therapeutic dose range is worrisome when it comes to the need for rapid control of systemic mold infections in immunocompromised patients and it underlines the need for a reliable solubilized dose formulation (Ref 10, 32). Further, any attmempt(s) to speed up the saturation of tissue levels of POSA by increasing the dose intensity will only be partially successful because of its unpredictable bioavailability, in the range of 50-60%, and an apparent saturation of intestinal drug absorption with increasing dose intensity (Ref 29).

A solvent system was discovered that provides a stock formulation that at 2-6 mg/mL, is stable (>90%) for at least three days (72 hours) at RT, and when diluted with an equal amount of a secondary aqueous diluent, such as normal saline (NS) or dextrose in water as preferred final diluents, the resulting use-formulation is stable at 2 mg/mL for at least 24 hours at RT.

The figures above demonstrate the stability of solubilized ITZA at RT, both in the stock-formulation and in the final use-formulation based on the preferred composite solvent systems H3 containing ITZA at approximately 4 mg/mL and when diluted with NS or dextrose in water to approximately 2 mg/mL, respectively. Specifically, ITZA was dissolved in the variant composite solvent vehicles of H3, and then diluted to appropriate concentrations with NS or 5% and 10% dextrose in water. Such composite solvent systems are not only suitable for exploration of prolonged (12 ±hours) infusion times, but also allow for convenient pharmaceutical handling when repeated infusions are desired. Such prolonged stability leaves an extensive margin of time for preparation and handling in the pharmacy and by the medical team prior to actual patient administration. Specifically, if a treatment dose of 2-5 mg/kg body weight is desired, a stock formulation of ITZA in the range of 2-10 mg/mL in our preferred composite solvent vehicles H3, variants of which are described, could be appropriately diluted in a similar volume of NS or other routinely available infusion fluid to achieve the desired final use-concentration. The clinician could then elect to infuse ITZA over either short or prolonged time periods without having to exchange bags of infusate that might be needed if the formulation had more limited physical stability and/or were subject to chemical degradation. Further, there should be no concern if pharmacy "service hours" are limited to the regular day-time service, since the final use-formulation can be prepared during the day-shift, and because of its extended stability in solution this would still conveniently allow for night-time administration.

Enhanced Solubility in Physiologically Acceptable Solvents

The solubility of ITZA was determined in several individual vehicles. Briefly, a known amount of ITZA drug, formulated as a powder (Sigma Inc., St Louis, Mo.), was equilibrated in the respective solvent at RT over 1-4 hours. An aliquot was removed, filtered, and prepared for HPLC to determine maximum solubility at room temperature. Based on the ITZA solubility in each vehicle, different solvents were mixed according to the cosolvency principle in an attempt to arrive at an enhanced stable solubility. Based partly on individual solvents' ability to solubilize the drug, different composite solvent systems were then evaluated relative to estimates to arrive at a stable stock formulation that could be mixed with a routinely available infusion fluid, such as normal saline (NS; 0.9% NaCl or 5-10% dextrose in water) and which would be useful in the clinical situation. We made the assumption, that either intermittent administration, or in rare cases, a prolonged infusion would be the preferred modes of administration, i.e., choosing an infusion schedule that would require the solvent vehicle to accept a dissolved drug concentration that could be infused in a clinically acceptable volume (preferably less than 1,000 mL total volume or approximately 500 mL/m$^2$ of body surface area [BSA]) and stable for at least (8-) 12 hours at RT. The stock formulation was then diluted with a final diluent, i.e. NS or D5W or DIOW, to yield a stable use-formulation. The desired range of the final use-formulation was between 1 and 5 mg/mL, as it would result in a final volume that could be safely and conveniently infused intravascularly.

Several water-miscible, physiologically-acceptable vehicles that would be compatible with human administration were examined (Table 1). The candidate solvents included acetic acid, Normal saline, dextrose in water polyoxyethylated castor oil, Propylene glycol, citric acid, Ethanol, HCl, PEG 400, benzyl alcohol, and finally, DMSO. Benzyl alcohol and acetic acid were the best primary solvents, whereas ITZA was very poorly soluble in the aqueous solvents. Ultimately, however, there would be a need to use a second/terminal aqueous diluent to make the infusate compatible with routine clinical handling. Several composite solvent vehicles were designed and examined; The preferred solvent vehicles, jointly referred to as "H3", were composed based on acidified alcohol and PEG400. The addition of acidified alcohol was intended to achieve a significant lowering of the pH to below normal physiological levels, contributing to keep the drug solubilized in an acidified, lipophilic infusate (the latter further accounted for by the addition of PEG400). These composite solvent vehicles allowed a stable solubility of ITZA at concentrations readily acceptable for infusion of doses previously shown to have significant antifungal/antimicrobial activity when repeated doses were administered in humans and domestic animals (Ref 10, 27, 29, 40-42, 45), and the drug was demonstrated to remain stable in solution for at least 24 hours at RT (FIG. 1).

HPLC Assay

The HPLC system was modified form Woestenberghs et al (Ref 52). Briefly, it utilized a C18 Nova-Pak analytical column with an average of 4-μm bead size; 150 mm×3.9 mm (Waters, Milford, Mass.), equipped with Waters 717 plus autosampler, a pump model 600E system controller (Waters), set to a flow rate of 1.0 ml/min. The detector was a Waters model 486 Tunable Fluorescence Detector in sequence with a Waters Millennium™ software package for HPLC (Waters, Milford, Mass.). It was set at 261 nm for Itraconazole (ITZA), 273 nm for mebendazole (MBZA), 230 nm for Ketoconazole (KZSA) and 259 nm for Fluconazole (FZSA). The isocratic mobile phase for ITZA, KZSA and MBZSA was a mixture of 60% acetonitrile in $H_2O$ plus 0.05% diethylamine. The isocratic mobile phase for FZSA was 30% acetonitrile in $H_2O$ plus 0.05% diethylamine. A standardized volume of 10-30 μL was injected into the HPLC column for quantitation of the respective azole analogues. Table 9 below summarizes the parameters used for the HPLC analysis.

TABLE 9

HPLC parameters

| Drug | Mobile phase* | Flow rate (ml/min) | Wavelength (nm) |
|---|---|---|---|
| Itraconazole | A | 1.0 | 261 |
| Posaconazole | A | 1.0 | 261 |
| Fluconazole | B | 1.0 | 259 |
| Mebendazole | A | 1.0 | 273 |
| Ketoconazole | A | 1.0 | 230 |

*A - 60:40 Acetonitrile:water + 0.05% Diethylamine B - 30:70 Acetonitrile:water + 0.05% Diethylamine The expected retention time for ITZA was 4.7-5.5 min and, as expected, varied somewhat with respect to which particular azole compound was assayed as shown in Table 8. The retention time for POSA was 2.5-3 min.

HPLC assay provides an accurate and sensitive detection system for low concentrations of ITZA (azole compounds) in solution, both protein-free mixtures and protein-containing fluids (such as clinically obtained samples, e.g. blood plasma), utilizing fluorescence detection in the UV spectrum. For the detection of ITZA and POSA, a wavelength of 261 was chosen, based on the inherent absorption and emission maxima of the ITZA molecule. This was varied as to which particular azole analog was examined (Table 9).

All chemicals were HPLC grade unless otherwise indicated. The mobile phase flow rate was 1.0 ml/min. The analytic system was based on previously established extraction and HPLC experience with ITZA as described by (Ref 52).

To avoid analytical interference from endogenous plasma proteins in the chromatogram when assaying ITZA in plasma samples, an extraction/purification step was performed, utilizing precipitation of protein material with acetonitrile. Briefly, plasma proteins were precipitated by adding acetonitrile to a final volume ratio plasma:acetonitrile of 1:2. The mixture was vortexed for 30 seconds and centrifuged for 5 min. at 14,000 rpm in an Eppendorff microcentrifuge. The deproteinated supernatant, containing ITZA, was injected into the HPLC to determine the drug concentration.

Examples of authentic ITZA chromatograms from the HPLC assay are shown in FIGS. 3A and 3B. FIG. 3 depicts two chromatograms obtained from the HPLC assay in the (protein-free) stability studies. The injected sample volume was 10 μL. The HPLC conditions are described above. In these panels the drug analyzed was from the stability study, where ITZA was dissolved in the prototype H3 solvent vehicles (a), and further diluted using NS as the final diluent (b). The HPLC retention time under the above conditions utilizing the C18 Nova-Pak column was 4.7-5.5 min. The assay was linear from 0.1 μg/mL to 100 μg/mL in protein-free solutions, i.e. the various solvent systems utilized in the formulation-feasibility and -stability studies (FIG. 2). FIG. 2 is the standard curve of ITZA concentration vs. area under the curve (AUC) (area under the curve, term used to denote the actual measured area of a peak in a chromatogram, and also for the area under the plasma concentration vs. time curve over several hours after administration of a drug to an animal or human being) for the high-pressure liquid chromatography (HPLC) assay used in the stability studies. The X-axis shows concentration in μg/ml, and the Y-axis shows the AUC. An analogous standard curve was prepared for the pharmacology study, see also below. The corresponding chromatograms obtained with POSA in the stability study are shown in FIG. 3d, when using the composite H3G solvent vehicle.

This HPLC assay consistently yielded high recovery and accuracy and a lower sensitivity limit of about 10-20 ng/mL, sufficient for the planned experiments. This HPLC technique was standardized and used for all stability studies without additional modifications, except as necessitated by assaying different azole-analogs (Table 9). For the in vivo plasma pharmacology study, the appearance of endogenous plasma protein-derived peaks in the chromatogram necessitated the addition of the described extraction/purification step, based on protein-precipitation with acetonitrile. For the analysis of ITZA and POSA concentrations in plasma ("protein-containing solutions"), see Example 3 below.

Example 2

Demonstration of In Vitro Stability and Other Properties of Some of the Novel Composite Solvent Vehicles In this example, stable ITZA and POSA formulations, that are suitable for human administration were evaluated. The chemical and physical stability of ITZA in composite solvent vehicles were established. Further, the solubility of ITZA in these composite solvent vehicles, when the final use aqueous diluents were NS or 5% and 10% dextrose in water, as representatives of clinically readily available infusion solutions, was established. This example also investigated the extended in vitro properties of one of these formulations, including its pH, hemolytic potential, and cytotoxic activity against a multitude of yeasts, and other molds/fungal strains, known to be pathogenic in immunocompromised humans and domestic animals, to establish that these prototype solvent system(s) is/are appropriate for systemic (e.g. intravascular) administration as therapy for infections sensitive to azole compounds in humans and other mammals.

Solubility Studies

An excess of ITZA as a powder was added to a multitude of chemical solvents (Table 1) at RT. Each mixture was intermittently vortexed, placed in a dark environment and checked visually for up to 4 hours for evidence of solubilization. Following centrifugation to remove solid particles, small samples were withdrawn after consecutive time intervals and the ITZA concentration was determined by HPLC as described.

A maximum equilibrium ITZA solubility of >100 mg/mL was achieved in pure acetic acid and Benzyl alcohol within 1 hour at RT.

There was insignificant solubility of ITZA in diluted acetic acid, $H_2O$, Normal saline, 5% Dextrose, Polyoxyethylated castor oil, Propylene glycol, 2 M citric acid, Ethanol, HCl, PEG400, and in 20% soybean lipid emulsion (Intralipid™) (Table 1). These latter individual solvents were not considered for further study.

In a second step the solubility in composite solvent vehicles was investigated, as based on the cosolveny principle. Based on these experiments we concluded that the solvent base preferably may contain up to 5% benzyl alcohol, and that an acidified non-aqueous, lipophilic, environment can be optimally created using the (clinically acceptable) cosolvents EtOH and PEG(-400) mixed with citric acid and HCl to create a low, subphysiological, pH necessary to maintain ITZA in solution when the secondary aqueous diluent is added. Thus, a preferred primary solvent vehicle for the continued investigations was composed of EtOH (6-27%, v/v), HCl (0.059 N), and Citric acid (1-5%) ±benzyl alcohol (0-5%, v/v), with PEG400, (10-90%, v/v).

At an ITZA concentration of 2-6 mg/mL in the composite solvent vehicles described above (prototype solvent vehicles), the ITZA was stable (more than 90%) for more than three days or 72 hours at RT. When primary stock solution of solvent/ITZA was diluted with NS or dextrose in water to 1-3 mg/mL respectively, ITZA remained stable with >95% recovered for more than 12 hours (FIG. 1, FIG. 3). Based on these findings, it was determined that the solubilized ITZA is stable enough to allow clinical routine handling and administration in these prototype solvent vehicles. For the purpose of this application, two preferred composite solvent vehicles were further contemplated and studied; First, one based around 2-4% (v/v) benzyl alcohol, and secondly, because of concern about reported toxicity related to benzyl alcohol exposure in human premature babies (Ref 47-51), a formulation that was void of benzyl alcohol and instead based entirely on a mixture of acidified EtOH in PEG400, using 10% dextrose in water as a preferred secondary diluent.

Stability of the Various Azole Formulations

The physical and chemical stability of the various formulations were studied as follows, using some of the above described preferred formulations as examples:

ITZA was dissolved at a final stock concentration of 2-6 mg/mL in benzyl alcohol with acidified EtOH/PEG-400 (prototype ITZA stock solvent vehicle) and incubated at RT and at 40° C. The resulting ITZA concentrations were measured by HPLC in samples taken immediately after solubilization, then hourly for 8 hours, and then at gradually increasing time intervals for up to several days (weeks), depending on the initial rate of solubilization/degradation in the respective solvent system.

The ITZA solubility differed markedly between different primary solvents. A solubility in excess of 100 mg/mL was reached using benzyl alcohol and glacial acetic acid. The acidified ethanol/PEG400, which was conducive for subsequent dilution in a terminal aqueous diluent, NS, such that the drug(s) can be safely and conveniently administered in a clinical situation without immediate precipitation when they are administered into the systemic blood circulation (the prototype ITZA/acidified EtOH-PEG solvents). These favored primary stock solvent vehicles were investigated further in the extended studies, as these formulations did not have any significant ITZA degradation recorded even over extended time (at least three days or 72 hours) at RT. In contrast, although both glacial acetic acid and HCl provided excellent solubility of ITZA, the drug started precipitating as soon as any secondary aqueous cosolvent/diluent was utilized. It was hypothesized that since ITZA is lipophilic, the benzyl alcohol with acidified EtOH/PEG400 would render the subsequent dilution in a purely aqueous vehicle (NS or 5% dextrose) possible without significant precipitation or rapid chemical degradation. The ITZA "stock" concentration in these composite solvents would be kept at a minimum of 2-6 mg/mL, with maintained stability and allowing for administration of a clinically active drug dose without resulting high doses of EtOH, PEG-400 or benzyl alcohol after dilution to a desired final use-concentration of 1.5-3 mg/mL (FIG. 1, FIG. 3). The hemolytic potential for the final use-formulation would be minimal, yet it should also provide negligible amounts of EtOH to the recipient. Thus, even at hypothetical clinical ITZA doses of 200-500 mg every 8-12 hours, the patient's total doses of the various cosolvents would clearly be within acceptable limits.

In summary, the stability of ITZA in the preferred acidified-EtOH±benzyl alcohol—PEG400 solvent system was excellent: after more than 3 days at RT at least 90% of the drug was intact, still in solution, when assayed by HPLC.

Hemolysis Studies In Vitro

A procedure simplified from Parthasarathy et al. was used to examine the hemolytic potential of a few selected formulations, and the $LD_{50}$ values of these most optimized formulations was constructed as previously described (Ref 53). Briefly, heparinized blood was mixed with an equal volume of Alsever's solution. This mixture was washed twice in PBS, and a 10% (volume per volume, v/v) erythrocyte/PBS solution was then prepared and mixed with increasing amounts of the preferred solvent (prototype solvent vehicle of acidified EtOH±benzyl alcohol with PEG400±NS) without ITZA. These resulting mixtures were incubated for 4 hours at 37° C. At the end of the incubation, the cells were pelleted at 10,000×g in an Eppendorf microcentrifuge, and after washing twice in NS, the pellet was resuspended and lysed using distilled water. The release of hemoglobin in the supernatant (i.e., hemolysis) was determined spectrophotometrically at a wavelength of 550 nm. Maximum lysis was measured against a reference erythrocyte solution that had been lysed by hypotonic shock. The hemolytic potential of the preferred stock- and final use-formulation was then evaluated as described. The results were plotted as the fraction of intact erythrocytes versus concentration (total volume percent) of the solvent vehicle. The total volume percent was defined as the volume percent of the solvent system in the mixture after addition of the erythrocyte suspension. This was done to simulate the dilution of the drug formulation in the blood stream after parenteral administration. Intact, healthy erythrocytes were defined as those capable of retaining their hemoglobin intracellularly after mixture with the solvent vehicle (Ref 53).

As shown in FIG. 4, the preferred stock-formulations showed a very low hemolysis-inducing potential when the complete vehicle was used in a fraction that was relevant for clinical administration.

The data derived from repeated experiments with the complete vehicle (prototype acidified EtOH/PEG400 solvent vehicle and NS) are summarized in FIG. 4. FIG. 4 is a graph showing the hemolytic potential of the final use formulation (-■-). The X-axis shows the solvent system as a fraction of the total volume tested The Y-axis shows the percent hemolysis. In conclusion, the preferred H3 solvent using acidified EtOH±benzyl alcohol with PEG400/NS complete (final-use) vehicle had very low hemolytic potential and should be completely safe for mammalian (preferably human) intravascular (and intracavitary, e.g. intraperitoneal or intrapleural, and intrathecal) administration.

In Vitro Cytotoxicity of ITZA

The antimicrobial/antifungal potential of selected solvent systems with and without ITZA was determined against several isolates of both yeast and different mold species. The findings confirm that the ITZA, POSA, KTZA and FZSA retain antifungal activity, while MBZSA as expected had no such activity (Tables below). The variant solvent systems are in themselves without any effect on mold- and yeast-proliferation.

TABLE 10

A. Yeasts
Tested drug dilution range 38 µg/mL to 0.03 µg/mL

| Candida cruzei (ATCC strain 6258) | | Candida parapsilosis | |
|---|---|---|---|
| Drug | MIC | Drug | MIC |
| ITZA | 0.07 | ITZA | 0.03 |
| MBZSA | all grew (no drug effect) | MBZSA | all grew |
| FZSA | all grew | FZSA | 1.2 |
| ITZA(ref 2) | 0.3 | ITZA(ref 2) | 0.15 |
| KZSA | 0.15 | KZSA | 0.03 |
| ITZA* | 0.15 | ITZA* | 0.07 |

ITZA(ref 2) is a second batch of ITZA dissolved in the basic test vehicle,
ITZA* is a control lot of ITZA dissolved in DMSO as a positive control Growth controls (negative controls, fungae grown in medium only) displayed excellent growth. Candida growth in medium with solvent vehicle without drug also displayed excellent growth.

B. Molds

Two hyaline molds were tested with a standard read out at 48 hrs:

Tested drug range: 75 µg/mL to 0.07 µg/mL
Aspergillus fumigatus (ATCC strain 90906) Aspergillus fumigatus (Clinical Lab isolate)

| Drug | MIC | Drug | MIC |
|---|---|---|---|
| ITZA | 1.2 | ITZA | 0.6 |
| MBZSA | all grew (no drug effect) | MBZSA | 5 |
| FZSA | all grew | FZSA | all grew |
| ITZA(Ref 2) | 0.6 | ITZA(Ref 2) | 0.3 |
| KZSA | 20 | KZSA | 20 |
| ITZA* | 0.6 | ITZA* | 0.3 |

For description of ITZA (Ref 2) and ITZA*, see above.

A. Extended mold testing

To further determine the antifungal activity of the compounds in the new formulation systems we investigated the efficacy of the various agents against additional strains of mucor and Aspergillus (9/-16-9/20/2010) (The Rhizomucor was a clinical isolate from a patient isolate) and the Aspergillus fumigatus (ATCC strain 90906) used was a repeat from the previously described experiment. Again, the susceptibility tests were set-up using the standardized test method (CLSI M38A). The used drugs were provided in the described H3 final use-formulation that has been previously described. All drugs were diluted in RPMI-Mops medium (YeastOne, Sensititer Lot 151416SA, expiration date January 2011).

As before two different molds were tested with a standard read out at 48 hr:

Drug dilution range 75 µg/mL to 0.07 µg/mL.

Aspergillus fumigatus (ATCC strain 90906) Zygomycete (Clinical Lab isolate, MDACC)

| Drug | MIC | Drug | MIC |
|---|---|---|---|
| ITZA | 1.2 | ITZA | 2.5 |
| MBZSA | all grew (no inhibition) | MBZSA | all grew |
| FZSA | all grew | FZSA | all grew |
| ITZA(Ref 2) | 0.3 | ITZA(Ref 2) | 2.5 |
| KZSA | 10 | KZSA | 38 |
| ITZA* | 0.3 | ITZA* | 2.5 |

All mold growth controls, including controls with solvent vehicle(s) without added azole drug, grew without inhibition as described before.

For description of ITZA (Ref 2) and ITZA*, see above.

Briefly, susceptibility tests were set-up using a standardized methodology (CLSI M38A standard). Drugs were diluted into RPMI-Mops medium (Yeast One Broth (Sensititer, product Y3462, Trek Diagnostic Systems, Cleveland, Ohio) Sensititer Lot number 151416SA-expiration date 2011-01). Two different strains of yeast were tested, the standardized evaluation/read out was performed at 24 hours after the start of each culture. The tests were repeated twice and all MIC (minimum inhibitory concentration) values are reported as an average of the three experiments.

TABLE 11

Stability of POSA in variant H3 Solvents

| POSA in H3d | RT | AUC |  | average mg/mL | % of 0 hr | POSA in H3d/5% Dextrose | RT | AUC |  | % of 0 hr |
|---|---|---|---|---|---|---|---|---|---|---|
| 0 hr | 2.554 | 400826 | 3.82 | 3.78 | 100 | 0 hr | 2.564 | 193985 | 1.75 | 100 |
|  | 2.554 | 393993 | 3.75 |  |  |  | 2.565 | 196323 | 1.77 |  |
|  | 2.558 | 397597 | 3.78 |  |  |  | 2.564 | 199974 | 1.81 |  |
| 2 hr | 2.571 | 385911 | 3.67 | 3.79 | 100 | 2 hr | 2.58 | 196729 | 1.77 | 100 |
|  | 2.571 | 400438 | 3.81 |  |  |  | 2.581 | 192890 | 1.74 |  |
|  | 2.575 | 408252 | 3.89 |  |  |  | 2.583 | 201970 | 1.83 |  |
| 4 hr | 2.608 | 419180 | 4.00 | 4.24 | 112 | 4 hr | 2.618 | 207424 | 1.88 | 111 |
|  | 2.609 | 433947 | 4.15 |  |  |  | 2.62 | 200171 | 1.81 |  |
|  | 2.613 | 475363 | 4.56 |  |  |  | 2.621 | 238841 | 2.20 |  |
| 6 hr | 2.631 | 438783 | 4.20 | 4.45 | 118 | 6 hr | 2.643 | 213853 | 1.95 | 109 |
|  | 2.632 | 451738 | 4.32 |  |  |  | 2.645 | 212355 | 1.93 |  |
|  | 2.635 | 501635 | 4.82 |  |  |  | 2.648 | 213037 | 1.94 |  |
| 8 hr | 2.678 | 437332 | 4.18 | 3.99 | 106 | 8 hr | 2.696 | 205638 | 1.86 | 102 |
|  | 2.682 | 395893 | 3.77 |  |  |  | 2.701 | 187614 | 1.68 |  |
|  | 2.687 | 421950 | 4.03 |  |  |  | 2.703 | 209511 | 1.90 |  |
| 24 hr | 2.932 | 400269 | 3.81 | 3.83 | 101 | 24 hr | 2.909 | 196815 | 1.78 | 103 |
|  | 2.932 | 393804 | 3.75 |  |  |  | 2.912 | 198214 | 1.79 |  |
|  | 2.934 | 411463 | 3.92 |  |  |  | 2.92 | 211982 | 1.93 |  |

| POSA in H3G | RT | AUC |  | Average mg/mL | % of 0 hr | POSA in H3G/5% Dextrose. | RT | AUC |  | % of 0 hr |
|---|---|---|---|---|---|---|---|---|---|---|
| 0 hr | 2.558 | 395039 | 3.76 | 3.70 | 100 | 0 hr | 2.564 | 195301 | 1.76 | 100 |
|  | 2.558 | 388090 | 3.69 |  |  |  | 2.567 | 194992 | 1.76 |  |
|  | 2.558 | 385218 | 3.66 |  |  |  | 2.565 | 187523 | 1.68 |  |
| 2 hr | 2.574 | 412117 | 3.93 | 3.78 | 102 | 2 hr | 2.583 | 202858 | 1.84 | 109 |
|  | 2.578 | 392475 | 3.73 |  |  |  | 2.584 | 200590 | 1.81 |  |
|  | 2.577 | 386425 | 3.67 |  |  |  | 2.586 | 220873 | 2.02 |  |
| 4 hr | 2.613 | 416905 | 3.98 | 4.23 | 114 | 4 hr | 2.622 | 211448 | 1.92 | 113 |
|  | 2.612 | 452197 | 4.33 |  |  |  | 2.625 | 210197 | 1.91 |  |
|  | 2.616 | 456664 | 4.37 |  |  |  | 2.627 | 222523 | 2.03 |  |
| 6 hr | 2.637 | 430900 | 3.98 | 4.23 | 114 | 6 hr | 2.65 | 194434 | 1.75 | 109 |
|  | 2.638 | 418489 | 4.33 |  |  |  | 2.654 | 212007 | 1.93 |  |
|  | 2.641 | 459396 | 4.37 |  |  |  | 2.653 | 220443 | 2.01 |  |
| 8 hr | 2.688 | 387222 | 3.68 | 3.57 | 97 | 8 hr | 2.706 | 189940 | 1.71 | 106 |
|  | 2.691 | 365952 | 3.47 |  |  |  | 2.711 | 208630 | 1.89 |  |
|  | 2.691 | 376511 | 3.57 |  |  |  | 2.715 | 211696 | 1.92 |  |
| 24 hr | 2.929 | 392249 | 3.73 | 3.65 | 99 | 24 hr | 2.919 | 197453 | 1.78 | 105 |
|  | 2.929 | 371428 | 3.52 |  |  |  | 2.924 | 199459 | 1.80 |  |
|  | 2.933 | 388985 | 3.70 |  |  |  | 2.927 | 205780 | 1.87 |  |

Example 3

Quantitative ITZA and POSA Analysis in Plasma and Pharmacology After IV Administration This example demonstrates that ITZA in a preferred variant composite solvent vehicles of H3 and mixed with blood or plasma may be recovered as native drug using quantitative extraction technology and HPLC assay, and that the ITZA and POSA concentrations remain in the fungitoxic range for in excess of one hour after IV administration of a dose of 5 mg/kg. It further indicates that the plasma pharmacokinetics after parenteral administration of ITZA and POSA in a preferred formulation in mice conforms to what can be expected based on the published pharmacology of oral ITZA and POSA. The estimated half-life of about 30 min of ITZA in our preliminary in vivo experiments appears significantly shorter than the 10+hours reported for use of oral ITZA (Ref 42, 45). However, it is highly likely that the 30 min half-life after a single IV dose reflects the initial blood-to-tissue distribution half-life, which is significantly shorter than the expected terminal elimination half-life (Ref 52). Further, oral drug administration may lead to slow intestinal absorption over many hours, such that the resulting observed plasma-concentration elimination curve/half-life reflects the net effects of absorption from gut to blood plus distribution from blood to tissues and finally metabolic degradation, all of which is additionally confounded by first-pass elimination of drug that passes through the portal vein to the liver before it reaches the systemic circulation.

Therefore, these different data sets cannot be directly compared, but the elimination half-life of 30 min after a short IV injection is in line with many other lipophilic drugs administered the same way. Interestingly, the POSA displayed a different pattern,; after an IV injection of 5 mg/kg over 4 min the peak concentration reached was about 3.2-3.3 µg/mL, with a half-life of 6-7 hr, which is in contrast to the estimated half-life of 15-30 hours after oral administration. Again, there is no direct comparison between repeated oral dosing in humans, and a single parenteral dose given in mice, but the data clearly demonstrate that after a single injection the resulting plasma concentrations reach and for extended time remain in a concentration range that has previously been demonstrated as fungi-static.

Quantitative Extraction of ITZA in Plasma

One milliliter of human blood plasma and whole blood was mixed with various amounts of the reformulated ITZA (final use-formulation, i.e. stock-formulation mixed 1:1 with normal saline), with human plasma or blood, with the reformulated drug constituting less than 3% of the total final volume, to yield a drug concentration of 0.2-3.0 µg/ml. The drug was then extracted from the plasma samples and analyzed by HPLC as described in Example 1. Briefly, 1 mL plasma was mixed with 1-2 volumes of acetonitrile to precipitate abundant plasma proteins and after centrifugation to remove the proteins the drug was then analyzed by HPLC with the ITZA (versus an alternative azole compound) detected spectrophotometrically at the respective wavelengths described above. The ITZA/POSA recovery from human plasma spiked to 9 µg/mL was calculated to be approximately 90%. As previously stated, the HPLC assay was linear in the interval from about 0.1 µg/mL to 100 µg/mL.

Parenteral ITZA and POSA: Experimental Protocol in Swiss Webster mice.

Unless specified, the analogous experiments were performed using POSA as an alternative to ITZA; Swiss Webster mice of both sexes with a body weight of 25-30 g were used for the in vivo pharmacology experiments (Harlan-Sprague-Dawley, Houston, Tex.). The animals were allowed a minimum of 7 days after arrival to accommodate to the new environment and allowed free access to commercial feed and tap water prior to and during the experimentation period. The animals were housed in an Association for the Assessment and Accreditation of Laboratory Animal Care International (AAALAC)-approved facility that meets the requirements of the USDA, NIH, and DHHS.

The ITZA dose of 5 mg/kg BW was determined to be a suitable test dose that could be administered to the mice as a slow (3-4 min) IV bolus injection without requiring sedation, but could be performed with only minimal physical restraint of the animals in a standard funnel-type cage.

The ITZA was formulated in the H3 solvent system described above as the preferred solvent to a stock concentration of 4-5 mg/mL and then diluted with NS (ratio 1:1) so the intended dose (5.0 mg/kg BW) could be injected in a tail vein in a total volume of approximately 100 µL. The ITZA concentrations of the final use-formulation were confirmed by HPLC prior to all drug administrations. No sedative premedication was used for the mice in this experiment to avoid the possible induction of microsomal liver enzymes that could modify ITZA metabolism. Thus, the animals were unanesthetized, being only physically restrained during and immediately following the drug injection.

Blood samples (0.5-1.0 mL) were drawn through cardiac puncture into heparinized tubes at selected time points prior to the drug infusion ("blank"), and from 5 min to 1 hour after drug injection for determination of ITZA concentrations, and for 5 min to about 7 hrs in the POSA experiment. The mice were exposed to 2% -4% isoflurane for general anesthesia. Blood samples were obtained through cardiac puncture and immediately deposited in heparinized microcentrifuge tubes. The blood was centrifuged at 2,000×g for 10 min at room temperature, the plasma was separated as described and stored at −80° C. until extracted and then assayed by HPLC, within 24 hours.

ITZA in Plasma and IV Drug Pharmacology Results

The drug extraction from plasma using acetonitrile precipitation of plasma proteins was essential to avoid interference from endogenous plasma protein components and to recover the maximum amount of drug. Authentic chromatograms from blank plasma (a), ITZA-spiked plasma (b), and one plasma-sample obtained from the current pharmacokinetic study (c) are shown in FIG. 6. This figure shows chromatograms of plasma samples extracted as described under Example 3 and then subjected to HPLC. FIG. 6a shows a blank plasma sample, FIG. 6b shows a plasma sample spiked with ITZA in the preferred composite solvent formulation (H3) to 9 µg/ml, and FIG. 6c shows a chromatogram from the pharmacology study, where a mouse was injected with ITZA at 5 mg/kg. The chromatogram was from a sample drawn 20 minutes after drug injection. In addition, FIG. 6d shows a blank mouse plasma sample, FIG. 6e shows a plasma sample spiked with POSA in the preferred composite solvent vehicle H3 G to 5 µg/mL, and FIG. 6f shows an actual chromatogram from a mouse plasma sample drawn 20 min after injection of POSA at 5 mg/kg in the in vivo experiment described above.

The ITZA retention time in this system was 4.7-5.5 min, and the POSA retention time was 2.4-3 min when using the C18 Nova-Pak column (see Example 1). The recovery of ITZA with the described technique was approximately 90% from human plasma spiked in vitro with 9 µg/mL of drug. The assay was linear after drug extraction from human plasma samples spiked in the concentration range from 0.1 µg/mL to 100 µg/mL. The limiting sensitivity was about 10-20 ng/mL when 10-30 µL was injected into the chromatograph. It should be recognized that the limiting factor here is the starting sample size, since it is technically very difficult to obtain more than 500 µL blood from an individual mouse. The inventor's documented data are intended to demonstrate the fact that IV injection of solubilized ITZA yields a plasma clearance pattern that is analogous with what can be expected when a pharmaceutically active drug is administered parenterally, and that intact ITZA can be recovered from blood samples obtained for at least one hour after drug administration. If it were desirable to optimize azole therapy in a clinical situation when treating an infection in a human or domestic animal it is quite conceivable that the precision and reproducible accuracy of the HPLC method could be significantly improved by extracting and analyzing larger volume samples, and by utilizing a larger part of the 2 mL injection loop in the HPLC system. Finally, it is possible to obtain a higher actual ITZA concentration in the injected sample by evaporating/reconstituting an eluted sample in a smaller volume prior to its injection into the HPLC. A standard curve was prepared in the range from 10 ng/mL to 50 µg/mL for the pharmacology experiment (not shown), and a good linear correlation (r=0.9999) was obtained between the actual plasma ITZA concentrations and the measured chromatographic peak AUC values.

The resulting data illustrate that the utilized novel ITZA (azole) formulation gives detectable, fungistatic ITZA (azole) plasma concentrations after injection of 5 mg/kg BW of ITZA or POSA in mice (FIGS. 7A and 7B). FIGS. 7A and 7B are graphs showing the change in plasma concentration over time, up to one hour, when 5 mg/kg of ITZA and POSA were injected in mice. The X-axis shows the time after dose in minutes. The Y-axis shows the azole concentration per µg/mL plasma. The apparent in vivo half-life of ITZA and POSA are in the range of 30 minutes and 6-7 hours, respectively under the conditions used with this formulation.

The injections were well tolerated, the azoles were injected slowly, over 3-4 min, to avoid possible adverse events such as cardiac arrhythmias or significant acute hemolytic events, none of which were documented in these experiments.

In summary, the data prove that the novel pharmaceutically acceptable, stable formulations of ITZA, POSA and other chemically related azole compounds can be used for intravascular administration in treatment of infections caused by microorganisms that are sensitive to these agents. The reformulated azoles retain their antimicrobial activity, which is exemplified by the strains of yeast and various molds that were used in the in vitro experiments and demonstrated to have their growth inhibited when exposed to ITZA (azole) formulated in the new prototype solvent vehicles. A preferred solvent vehicle is physiologically compatible with intravascular administration and was used as an illustration to demonstrate in the mouse model that the injection of ITZA and POSA in this solvent system was well accepted and conferred insignificant acute solvent system toxicity. The injection of this formulation in mice (5.0 mg/kg BW) yielded ITZA/POSA plasma concentrations that remained in the fungistatic range for well in excess of one hour, extrapolated from the slope of the elimination curve over the first hour after injection.

The data for the preferred variant final use-formulations of H3, conclusively prove that it is now feasible to re-introduce ITZA, and to introduce POSA, for parenteral administration in clinical therapy of infections sensitive to these agents, and demonstrate that also POSA can be safely and completely dissolved and introduced into the systemic circulation through intravascular administration. This can be expected to result in the predictable and reproducible attainment of greatly improved antifungal activity. These results also give a reasonable expectation of insignificant normal organ toxicity from the composite solvent vehicles. In particular, it is possible that serious hypersensitivity reactions may be completely avoided with these formulations, and if these composite vehicles H3D and H3G are favored, there should be no reason for concern even if the drugs are administered to premature babies or to seriously ill adults with suboptimal hepatic metabolic activity that may impair the individual's ability to adequately metabolize benzyl alcohol.

The novel solvent systems improve not only the clinical safety of azole-based anti-microbial (-infectious) therapy, but also to make it possible to further optimize the use of these important drugs in the treatment of fungal and other infections in immunocompromised patients that may have suboptimal bioavailability of orally administered drugs due to intestinal compromise and an accompanying inability to maintain proper oral nutrition. Embodiments of the invention may also be used when treating patients with anti-cancer chemotherapy who are at increased risk for systemic fungal infections, such as those undergoing conditioning treatment preceding hemopoietic stem cell transplantation.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

References

The following references, to the extent that they provide exemplary, procedural or other details supplementary to those set forth herein, are specifically incorporated herein by reference.

1. Baddley J W, Marr K A, Andes D R, Walsh T J, Kauffman C A, Kontoyiannis D P, Ito J I, Balajee S A, Pappas P G, Moser S A. Patterns of susceptibility of *Aspergillus* isolates recovered from patients enrolled in the Transplant-Associated Infection Surveillance Network. *J Clin Microbiol.* 2009; 47(10):3271-3275.
2. Campo M, Lewis R E, Kontoyiannis D P. Invasive fusariosis in patients with hematologic malignancies at a cancer center: 1998-2009. *J Infect. Dis* 2010; 60(5):331-337.
3. Chen S C, Playford E G, Sorrell T C. Antifungal therapy in invasive fungal infections. *Curr Opin Pharmacol.* 2010; 10(5):522-530.
4. Dutkiewicz R, Hage C A. Aspergillus infections in the critically ill. *Proc Am Thorac Soc.* 2010; 7(3):204-209.
5. Evans S E. Coping with Candida infections. *Proc Am Thorac Soc.* 2010; 7(3):197-203.
6. Glockner A, Karthaus M. Current aspects of invasive candidiasis and aspergillosis in adult intensive care patients. *Mycoses.* 2010; e-pub.
7. Hicheri Y, Toma A, Maury S, Pautas C, Mallek-Kaci H, Cordonnier C. Updated guidelines for managing fungal diseases in hematology patients. *Expert Rev Anti Infect Ther.* 2010; 8(9):1049-1060.
8. Hsu L Y, Ng E S, Koh L P. Common and emerging fungal pulmonary infections. *Infect Dis Clin North Am.* 2010; 24(3):557-577.
9. Ito J I, Kriengkauykiat J, Dadwal S S, Arfons L M, Lazarus H M. Approaches to the early treatment of invasive fungal infection. *Leuk Lymphoma.* 2010; 51(9):1623-1631.
10. Jang S H, Colangelo P M, Gobburu J V. Exposure-response of posaconazole used for prophylaxis against invasive fungal infections: evaluating the need to adjust doses based on drug concentrations in plasma. *Clin Pharmacol Ther.* 2010; 88(1): 115-119.
11. Kim A, Nicolau D P, Kuti J L. Hospital costs and outcomes among intravenous antifungal therapies for patients with invasive aspergillosis in the United States. *Mycoses.* 2010; e-pub.
12. Lehrnbecher T, Attarbaschi A, Duerken M, Garbino J, Gruhn B, Kontny U, Luer S, Phillips R, Scholz J, Wagner H J, Wiesel T, Groll A H. Posaconazole salvage treatment in paediatric patients: a multicentre survey. *Eur J Clin Microbiol Infect Dis.* 2010; 29:1043-1045.
13. Lewis R E, Kontoyiannis D P. Invasive aspergillosis in glucocorticoid-treated patients. *Med Mycol.* 2009; 47 Suppl 1:S271-281.
14. Lortholary O, Obenga G, Biswas P, Caillot D, Chachaty E, Bienvenu A L, Cornet M, Greene J, Herbrecht R, Lacroix C, Grenouillet F, Raad I, Sitbon K, Troke P. International retrospective analysis of 73 cases of invasive fusariosis treated with voriconazole. *Antimicrob Agents Chemother.* 2010; 54(10):4446-4450.
15. Pappas P G, Alexander B D, Andes D R, Hadley S, Kauffman C A, Freifeld A, Anaissie E J, Brumble L M, Herwaldt L, Ito J, Kontoyiannis D P, Lyon G M, Marr K A, Morrison V A, Park B J, Patterson T F, Perl T M, Oster R A, Schuster M G, Walker R, Walsh T J, Wannemuehler K A, Chiller T M. Invasive fungal infections among organ transplant recipients: results of the Transplant-Associated Infection Surveillance Network (TRANSNET). *Clin Infect Dis.* 2010; 15;50(8):1101-1111.
16. Person A K, Kontoyiannis D P, Alexander B D. Fungal infections in transplant and oncology patients. *Infect Dis Clin North Am.* 2010; 24(2):439-459.

17. Singh N, Limaye A P, Forrest G, Safdar N, Munoz P, Pursell K, Houston S, Rosso F, Montoya J G, Patton P, Del Busto R, Aguado J M, Fisher R A, Klintmalm G B, Miller R, Wagener M M, Lewis R E, Kontoyiannis D P, Husain S. Combination of voriconazole and caspofungin as primary therapy for invasive aspergillosis in solid organ transplant recipients: a prospective, multicenter, observational study. *Transplantation.* 2006; 81(3):320-326.
18. Torres H A, Hachem R Y, Chemaly R F, Kontoyiannis D P, Raad, I I. Posaconazole: a broad-spectrum triazole antifungal. *Lancet Infect Dis.* December 2005; 5(12):775-785.
19. Ullmann A J, Lipton J H, Vesole D H, Chandrasekar P, Langston A, Tarantolo S R, Greinix H, Morais de Azevedo W, Reddy V, Boparai N, Pedicone L, Patino H, Durrant S. Posaconazole or Fluconazole for phophylaxis in severe graft-versus-host disease *N Engl J Med.* 2007; 356(4):335-347.
20. Vehreschild J J, Ruping M J, Wisplinghoff H, Farowski F, Steinbach A, Sims R, Stollorz A, Kreuzer KA, Hallek M, Bangard C, Comely O A. Clinical effectiveness of posaconazole prophylaxis in patients with acute myelogenous leukaemia (AML): a 6 year experience of the Cologne AML cohort. *J Antimicrob Chemother.* 2010; 65(7):1466-1471.
21. Walsh T J, Driscoll T, Milligan P A, Wood N D, Schlamm H, Groll A H, Jafri H, Arrieta A C, Klein N J, Lutsar I. Pharmacokinetics, safety, and tolerability of voriconazole in immunocompromised children. *Antimicrob Agents Chemother.* 2010; 54(10):4116-4123.
22. Wingard J R, Carter S L, Walsh T J, et al. Randomized double-blind trial of fluconazole versus voriconazole for prevention of invasive fungal infection (IFI) after allo hematopoietic cell transplantation (HCT). *Blood.* September 8.
23. Winston D J, Bartoni K, Territo M C, Schiller G J. Efficacy, Safety, and Breakthrough Infections Associated with Standard Long-Term Posaconazole Antifungal Prophylaxis in Allogeneic Stem-Cell Transplant Recipients. *Biol Blood Marrow Transplant.* 2010, e-pub.
24. Greer N D. Posaconazole (Noxafil): a new triazole antifungal agent. *Baylor Univ Med Center Proc.* 2007; 20:188-196.
25. Carrillo-Munoz A J, Quindos G, Ruesga M, et al. Antifungal activity of posaconazole compared with fluconazole and amphotericin B against yeasts from oropharyngeal candidiasis and other infections. *The Journal of antimicrobial chemotherapy* 2005; 55(3):317-9.
26. Dodds Ashley E S, Alexander B D Posaconazole. *Drugs of today* 2005; 41(6):393-400.
27. Groll A H, Walsh T J Antifungal efficacy and pharmacodynamics of posaconazole in experimental models of invasive fungal infections. *Mycoses* 2006; 49 Suppl 1:7-16.
28. Notheis G, Tarani L, Costantino F, et al. Posaconazole for treatment of refractory invasive fungal disease. *Mycoses* 2006; 49 Suppl 1:37-41.
29. Courtney R, Pai S, Laughlin M, Lim J, Batra V. Pharmacokinetics, safety, and tolerability of oral posaconazole administered in single and multiple doses in healthy adults. *Antimicrobial Agents and Chemotherapy* 2003; 47(9):2788-95.
30. Dodds-Ashley E. Management of drug and food interactions with azole antifungal agents in transplant recipients. *Pharmacotherapy.* 2010; 30(8):842-854.
31. Benet L Z, Sheiner L B. Pharmacokinetics: The dynamics of drug absorption, distribution, and elimination. In: Goodman Gilman A, Goodman L S, Rall T W, Murad F. (Eds.). Goodman and Gilman's The Pharmacological Basis of Therapeutics. 7th Edition. MacMillan Publishing Co. New York, N.Y. 1985; P. 8.
32. Zhou H, Goldman M, Wu J, Woestenborghs R, Hassell A E, Lee P, Baruch A, Pesco-Koplowitz L, Borum J, Wheat L J. A pharmacokinetic study of intravenous itraconazole followed by oral administraiton of itraconazole capsules in patients with advanced human immunodeficiency virus infection. *Clin Pharmacol.* 1998; 38(7):593-602.
33. Cserháti T. Alykl ethoxylated and alkylphenol ethoxylated nonionic surfactants: interaction with bioactive compounds and biological effects. *Environ Health Perspec.* 1995; 103(4):358-364.
34. Dimitrijevic D, Shaw A J, Florence A T. Effects of some non-ionic surfactants on transepithelial permeability in Caco-2 cells. *J Pharm Pharmacol.* 2000; 52(5):157-162.
35. Warisnoicharoen W, Lansley A B, Lawrence M J. Toxicological evaluation of mixtures of nonionic surfactants, alone and in combination with oil. *J Pharm Sci.* 2003; 92(4):850-868.
36. Gelderblom H, Verweij J, Nooter K, Sparreboom A. Cremophor E L: the drawbacks and advantages of vehicle selection for drug formulation. *Eur J Cancer.* 2001; 37(13):1590-1598.
37. Coors E A, Seybold H, Merk H F, Mahler V. Polysorbate 80 in medical products and nonimmunologic anaphylactic reactions. *Ann Allergy Asthma Immunol.* 2005; 95(6):593-599.
38. Tamilvanan, S. Oil-in-water lipid emulsions: implications for parenteral and ocular delivering systems. *Prog Lipid Res.* 2004; 43(6):489-533.
39. Driscoll, D. Safety of parenteral infusions in the critical care setting. *Advanced Studies in Medicine.* 2002; 2(9): 338-342.
40. Boothe D M, Herring I, Calvin J, Way N, Dvorak J. Itraconazole disposition after single oral and intravenous and multiple oral dosing in healthy cats. *Am J Vet Res.* 1997; 58(8):872-77.
41. Davis J L, Salmon J H, Papich M G. Pharmacokinetics and tissue distribution of itraconazole after oral and intravenous administration to horses. *Am J Vet Res* 2005; 66(10):1694-1701.
42. Willems L, Van der Geest R, de Beule K. Itraconazole oral solutions and intravenous formulations; a review of pharmacokinetics and pharmacodynamics. *J Clin Pharm Ther.* 2001; 26(3): 159-169.
43. Spiegel A. J. Noseworthy M. N. Use of nonaqueous solvents in parenteral products. *J. Pharm. Sci.* 1963; 52:917-927.
44. Yalkowsky S. H., Roseman T. J. Solubilization of drugs by cosolvents. In: Yalkowsky S. H. (Ed.): Techniques of solubilization of drugs. 1981; Pp. 91-134. Marcel Dekker Inc., New York, N.Y.
45. Van de Velde V J, Van Peer A P, Heykants J J, Woestenborghs R J, Van Rooy P, De Beule K L, Cauwenbergh G F. Effect of food on the pharmacokinetics of a new hydroxypropyl-beta-cyclodextrin formulation of itraconazole. *Pharmacotherapy* 1996; 16(3):424-428.
46. Robertson R: Common poisonings. In: Wyngarden J B, and Smith L H (Eds.) Cecil. Textbook of Medicine. WB Saunders Company, Philadelphia, Pa. 1988. Pp. 140-145.
47. Neonatal deaths associated with use of benzyl alcohol. MMWR Weekly Report 1982; 31:290-91.

48. American Academy of Pediatrics Committee on Fetus and Newborn. Benzyl alcohol: toxic agent in neonatal units. *Pediatrics* 1983; 72:356-58.
49. Brown W J, Bulst N R, Gipson H, Huston R K, Kennaway N G. Fatal benzyl alcohol poisoning in a neonatal intensive care unit. *Lancet* 1982;1(8283):1250.
50. Menon P A, Thach B T, Smith C H, Landt M, Roberts J L, Hillman RE, Hillman L S. Benzyl alcohol toxicity in a neonatal intensive care unit. *Am J Perinatol* 1984; 1(4):288-92.
51. LeBel M, Ferron L, Masson M, Pichette J, Carrier C. Benzyl alcohol metabolism and elimination in neonates. *Dev Pharmacol Ther.* 1988; 11(6):347-56.
52. Woestenborghs R, Lorreyne W, Heykants J. Determination of itraconazole in plasma and animal tissues by high-performance liquid chromatography. *J Chromatogr.* 1987; 413:332-337.
53. Parthasarathy R, Sacks P G, Harris D, Brock H, Mehta K. Interaction of liposome-associated all-trans-retinoic acid with squamous carcinoma cells. *Cancer Chemother. Pharmacol.* 1994; 34(3):527-34.
54. Gibaldi M, Perrier D. Noncompartmental Analysis based on statistical moment theory. In: Pharmacokinetics, 2d Ed, Rev. and expanded, New York, N.Y., Marcel Dekker, 1982; 409-416.

Abbreviations Used in this Application
AAALAC—Association for the Assessment and Accreditation of Laboratory Animal Care International
ATCC—American Tissue Culture Collection, Rockville, Md.
AUC—area under the curve, term used to denote the actual measured surface area of a peak in a chromatogram, and also for the area under the plasma concentration vs. time curve over several hours after administration of a drug to an animal or human being as a measure of total systemic drug exposure.
BSA—Body surface area.
BW—Body weight.
CLSI—Clinical and Laboratory Standards Institute (here, providing Standards for Laboratory microbial susceptibility testing).
$D_5W$—5% dextrose in water.
$D_{10}W$—10% dextrose in water
DMSO—Dimethylsulfoxide.
DNA—Deoxyribonucleic acid.
DHHS—Department of Health and Human Services.
EtOH—Ethanol.
FDA—United States Food and Drug Administration.
FZSA—Fluconazole
HCl—Hydrochloric acid.
HPLC—High-pressure liquid chromatography.
Intralipid™—Brand name of an aqueous lipid emulsion made primarily from soybean oil and marketed for parenteral nutrition available from The soybean lipid emulsion was freeze-dried before use as a solvent in the ensuing studies and is referred to as "lipid" in this text.
ITZA—Itraconazole
KZSA—Ketoconazole
Liposyn™—Brand name of an aqueous lipid emulsion made primarily from soybean oil and marketed for parenteral nutrition available from Abbott (Abbott Park, Ill.). The soybean lipid emulsion was freeze-dried before use as a solvent in the ensuing studies and is referred to as "lipid" in this text.
MBZA—Mebendazole
MIC—Minimum inhibitory concentration.
NCI—National Cancer Institute.
NIH—National Institute of Health.
nm—nanometer.
NS—Normal saline (150 mM NaCl in water).
PBS—Phosphate-buffered saline (Dulbecco's formulation, pH 7.4).
PEG—and PEG-400/PEG400- Polyethylene glycol-400 (i.e. with an average molecular weight of 400 Daltons)
PG—Propylene glycol.
POSA—Posaconazole
RPMI-Mops—Standardized tissue culture medium buffered with Mops buffer (3-(N-morpholino)propanesulfonic acid, pH 7.2).
RT—Room temperature (22° C.).
RT—retention Time in the HPLC assay; used separately where indicated.
USDA—US Department of Agriculture.

The invention claimed is:

1. A clinically acceptable infusion fluid comprising a composition diluted with an infusion fluid selected from the group consisting of normal saline, dextrose in water, and a lipid-based infusion emulsion fluid, wherein the composition is a pharmaceutical composition suitable for parenteral administration comprising an azole antifungal pharmaceutical agent and a first solvent, said first solvent comprising a) an alcohol component selected from benzyl alcohol and/or acidified ethanol, and b) a polyethylene glycol solvent (PEG), wherein the azole agent is dissolved in said first solvent, wherein the composition is essentially free of non-ionic surfactants and particulates and comprises less than 5% water (v/v).

2. The clinically acceptable infusion fluid of claim 1, wherein said infusion fluid is dextrose in water.

3. The clinically acceptable infusion fluid of claim 1, wherein said fluid comprises between 1 mg/ml and 5 mg/ml of the azole agent after dilution in said infusion fluid.

4. The clinically acceptable infusion fluid of claim 1 wherein said azole pharmaceutical agent is stable for at least 12 hours at room temperature.

5. The clinically acceptable infusion fluid of claim 1, wherein the composition is further defined as comprising less than 3% water (v/v).

6. The clinically acceptable infusion fluid of claim 5, wherein the composition is further defined as comprising less than 1% water (v/v).

7. The clinically acceptable infusion fluid of claim 6, wherein the composition is further defined as essentially free of water.

8. The clinically acceptable infusion fluid of claim 1, wherein said first solvent of the composition comprises both acidified ethanol and benzyl alcohol.

9. The clinically acceptable infusion fluid of claim 1, wherein the first solvent of the composition comprises acidified ethanol.

10. The clinically acceptable infusion fluid of claim 9, wherein the acidified ethanol of the composition is further defined as a combination of ethanol and an acid, and the first solvent has a pH of from about 1 to about 5.

11. The clinically acceptable infusion fluid of claim 10, wherein the first solvent of the composition has a pH of from about 3 to about 4.

12. The clinically acceptable infusion fluid of claim 10, wherein the acid of the composition is HCl, citric acid, acetic acid or glutamic acid.

13. The clinically acceptable infusion fluid of claim 1, wherein the ratio of PEG to alcohol in the composition is from 27 to 2 (v/v).

14. The clinically acceptable infusion fluid of claim 13, wherein the ratio of PEG to alcohol in the composition is from 12 to 8 (v/v).

15. The clinically acceptable infusion fluid of claim 1, wherein said PEG of the composition is selected from the group consisting of PEG-100, PEG-200, PEG-300, PEG-400 and PEG-800.

16. The clinically acceptable infusion fluid of claim 15, wherein the polyethylene glycol of the composition is PEG-400.

17. The clinically acceptable infusion fluid of claim 1, wherein the first solvent of the composition comprises from 10% to 90% (v/v) PEG.

18. The clinically acceptable infusion fluid of claim 17, wherein the first solvent of the composition comprises from 30% to 90% (v/v) PEG.

19. The clinically acceptable infusion fluid of claim 1, wherein the first solvent of the composition comprises from 40% to 80% (v/v) PEG.

20. The clinically acceptable infusion fluid of claim 1, wherein the alcohol component of the composition is from 1% to 99% of the first solvent (v/v).

21. The clinically acceptable infusion fluid of claim 20, wherein the alcohol component of the composition is from 5% to 60% of the first solvent (v/v).

22. The clinically acceptable infusion fluid of claim 21, wherein the alcohol component of the composition is from 10% to 40% of the first solvent (v/v).

23. The clinically acceptable infusion fluid of claim 1, wherein the azole pharmaceutical agent of the composition is an imidazole, triazole or thiazole.

24. The clinically acceptable infusion fluid of claim 23, wherein the azole pharmaceutical agent of the composition is miconazole, ketoconazole, clotrimazole, econazole, omoconazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole or abafungin.

25. The clinically acceptable infusion fluid of claim 24, wherein the azole agent of the composition is itraconazole.

26. The clinically acceptable infusion fluid of claim 24, wherein the azole agent of the composition is posconazole.

27. The clinically acceptable infusion fluid of claim 1, wherein said composition comprises between 3 mg/ml to 25 mg/ml of the azole pharmaceutical agent.

\* \* \* \* \*